US012594223B2

(12) United States Patent
Reinshagen et al.

(10) Patent No.: US 12,594,223 B2
(45) Date of Patent: Apr. 7, 2026

(54) GRADIENT COMPOSITION ZIRCONIA DENTAL MATERIALS

(71) Applicant: Ivoclar Vivadent AG, Schaan (LI)

(72) Inventors: Jörg Reinshagen, Pforzheim (DE);
Henning Meyhöfer, Stuttgart (DE);
Frank Rothbrust, Röns (AT)

(73) Assignee: Ivoclar Vivadent AG, Schaan (LI)

( * ) Notice: Subject to any disclaimer, the term of this
patent is extended or adjusted under 35
U.S.C. 154(b) by 1054 days.

(21) Appl. No.: 17/620,592

(22) PCT Filed: Aug. 16, 2019

(86) PCT No.: PCT/EP2019/072067
§ 371 (c)(1),
(2) Date: Dec. 17, 2021

(87) PCT Pub. No.: WO2021/032272
PCT Pub. Date: Feb. 25, 2021

(65) Prior Publication Data
US 2022/0347060 A1     Nov. 3, 2022

(51) Int. Cl.
| | |
|---|---|
| *A61K 6/00* | (2020.01) |
| *A61K 6/02* | (2006.01) |
| *A61K 6/807* | (2020.01) |
| *A61K 6/818* | (2020.01) |
| *A61K 6/822* | (2020.01) |
| *C04B 41/00* | (2006.01) |
| *C04B 41/50* | (2006.01) |
| *C04B 41/51* | (2006.01) |
| *C04B 41/88* | (2006.01) |

(52) U.S. Cl.
CPC .............. *A61K 6/818* (2020.01); *A61K 6/807*
(2020.01); *A61K 6/822* (2020.01)

(58) Field of Classification Search
CPC ............................ A61K 6/818; A61K 6/822;
C04B 2235/3224; C04B 2235/3227;
C04B 35/48
See application file for complete search history.

(56) References Cited

U.S. PATENT DOCUMENTS

| | | |
|---|---|---|
| 2012/0034471 A1 | 2/2012 | Peterson |
| 2015/0374465 A1 | 12/2015 | Bürke et al. |
| 2018/0263863 A1* | 9/2018 | Kim ...................... A61K 6/822 |
| 2019/0127285 A1 | 5/2019 | Guillon et al. |
| 2019/0381769 A1 | 12/2019 | Reinshagen et al. |

FOREIGN PATENT DOCUMENTS

| | | |
|---|---|---|
| CN | 103058655 A | 4/2013 |
| EP | 2889279 A1 | 7/2015 |
| JP | 2018052806 A | 4/2018 |

OTHER PUBLICATIONS

CN103058655 machine translation (Year: 2013).*

* cited by examiner

*Primary Examiner* — Cameron K Miller
(74) *Attorney, Agent, or Firm* — Hodgson Russ LLP

(57) ABSTRACT
Provided are pre-sintered and sintered zirconia dental
ceramic materials. The materials have a gradient in yttria
content. The materials may have a gradient in one or more
physical/mechanical property and/or one or more optical
property. The materials may be made by mixing at least two
zirconia ceramic powders having different yttria content. A
sintered zirconia dental ceramic material may be in the form
of a dental article.

33 Claims, 39 Drawing Sheets sintered strength: ≥ 600 MPa
(ISO6872:2015)
sintered Hardness HV20: 12000 – 14000 MPa
(ISO14705:2016)
sintered density: ≥ 6.04 g cm⁻³ (99.7%)
Fracture Toughness: ≥ 2.2 MPa m$^{1/2}$ sintered strength: ≥ 1100 MPa
(ISO6872:2015)
sintered Hardness HV20: 12000 – 14000 MPa
(ISO14705:2016)
sintered density: ≥ 6.065 g cm⁻³ (99.7%)
Fracture Toughness: ≥ 4.5 MPa m$^{1/2}$

| Description | Unit | Effective Values |
|---|---|---|
| Presintered density | g cm$^{-3}$ | 3.236 - 3.536 |
| Enlargement Factor | --- | 1.210 – 1.235 |
| Hardness HV2.5 | MPa | 550 - 750 |
| Raw strength | MPa | 40 - 60 |
| Distortion factor | --- | < 0.2 |

Figure 7

| Description | Unit | Effective Values |
|---|---|---|
| Final density | g cm$^{-3}$ | > 6.065 |
| Enlargement Factor | --- | 1.210 – 1.235 |
| Hardness HV20 | MPa | 13000 |
| Final strength (Dentine as milled/as fired) | MPa | > 900 |
| Final strength (Dentine polished) | MPa | > 1300 |
| Final strength (Incisal) | MPa | > 650 |
| $K_{IC}$ (Dentine) | MPa m$^{1/2}$ | 5 |
| $K_{IC}$ (Incisal) | MPa m$^{1/2}$ | ~2.5 - 3 |

Figure 8

Transition Vol.-Content and Grainsize of Example 1
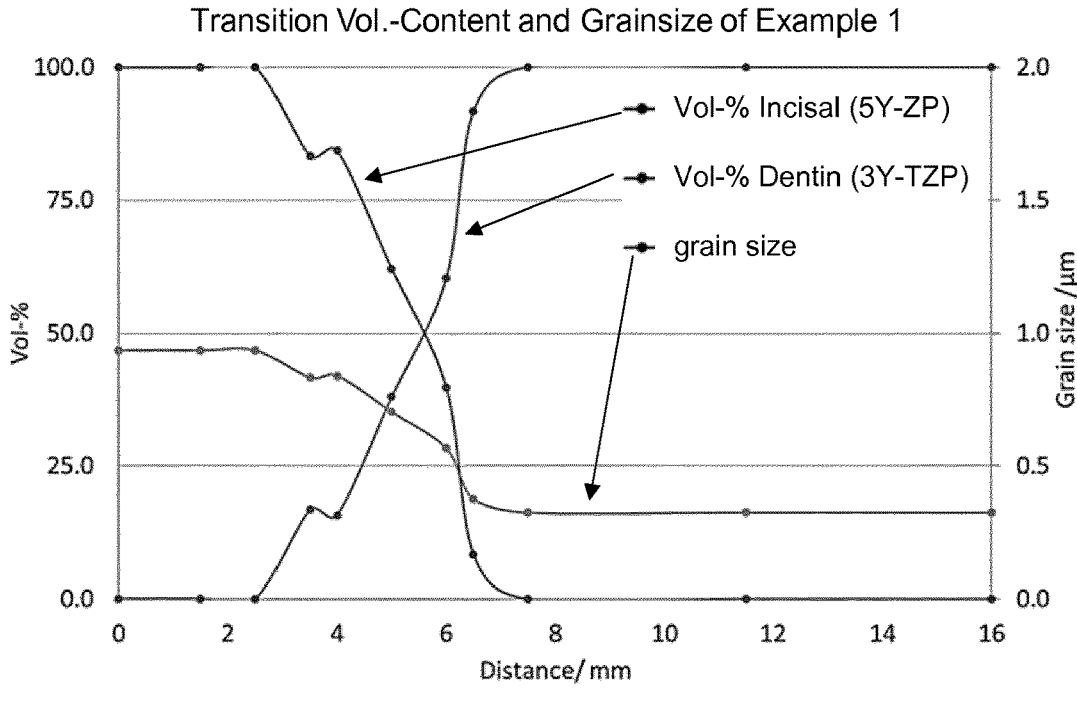
Corrected / interpolated
Transition Vol.-Content and Grainsize of Example 1
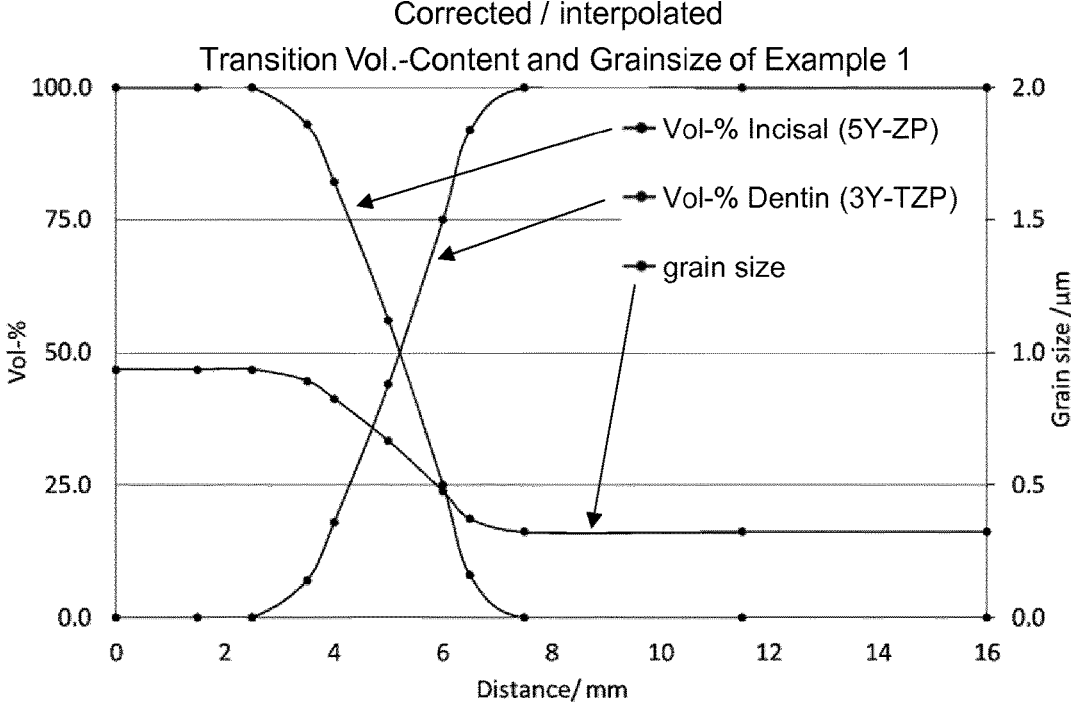
Figure 9

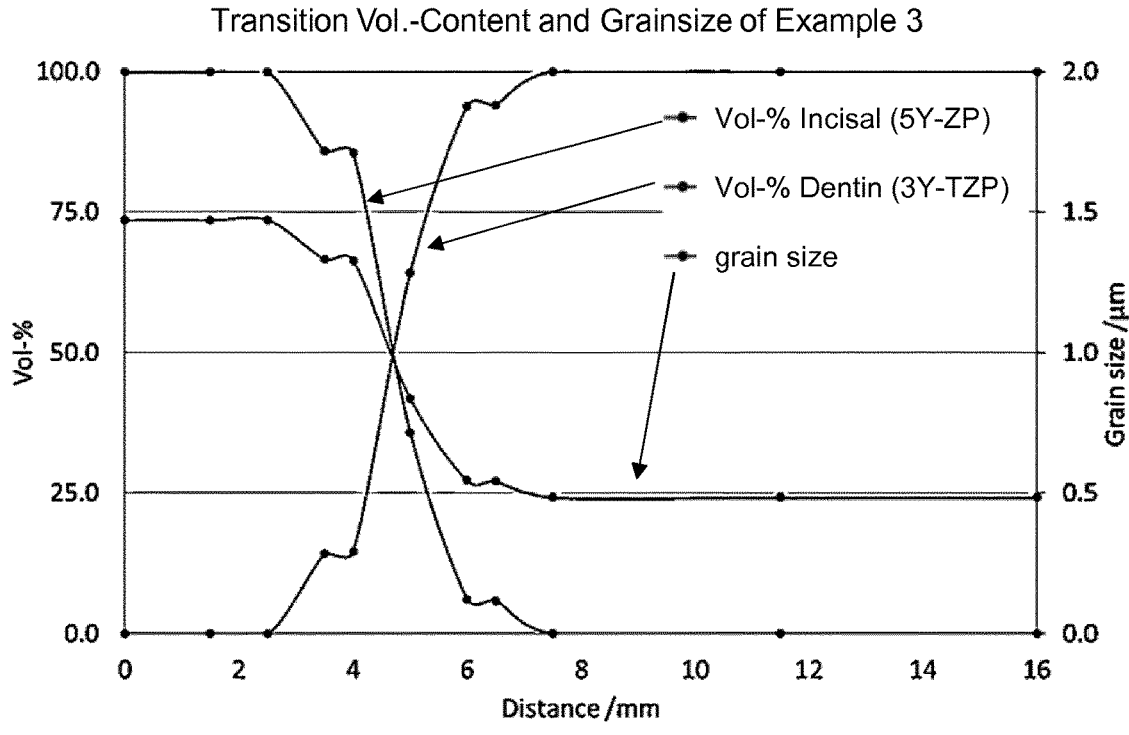
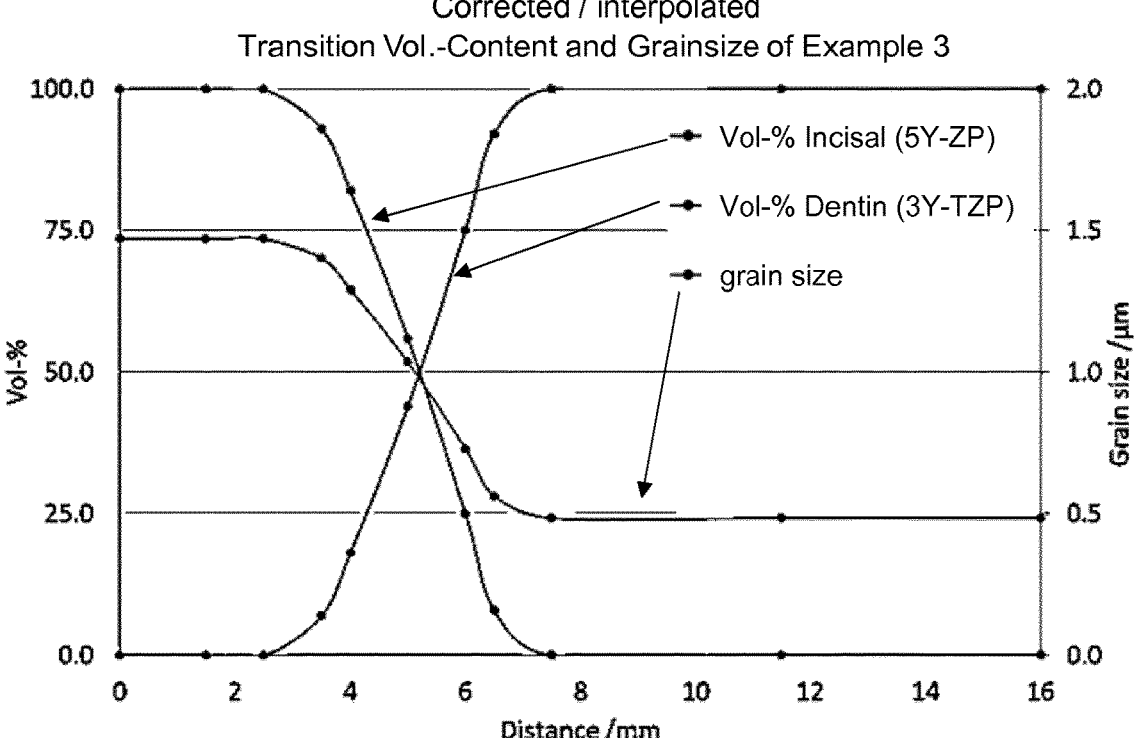
Figure 10

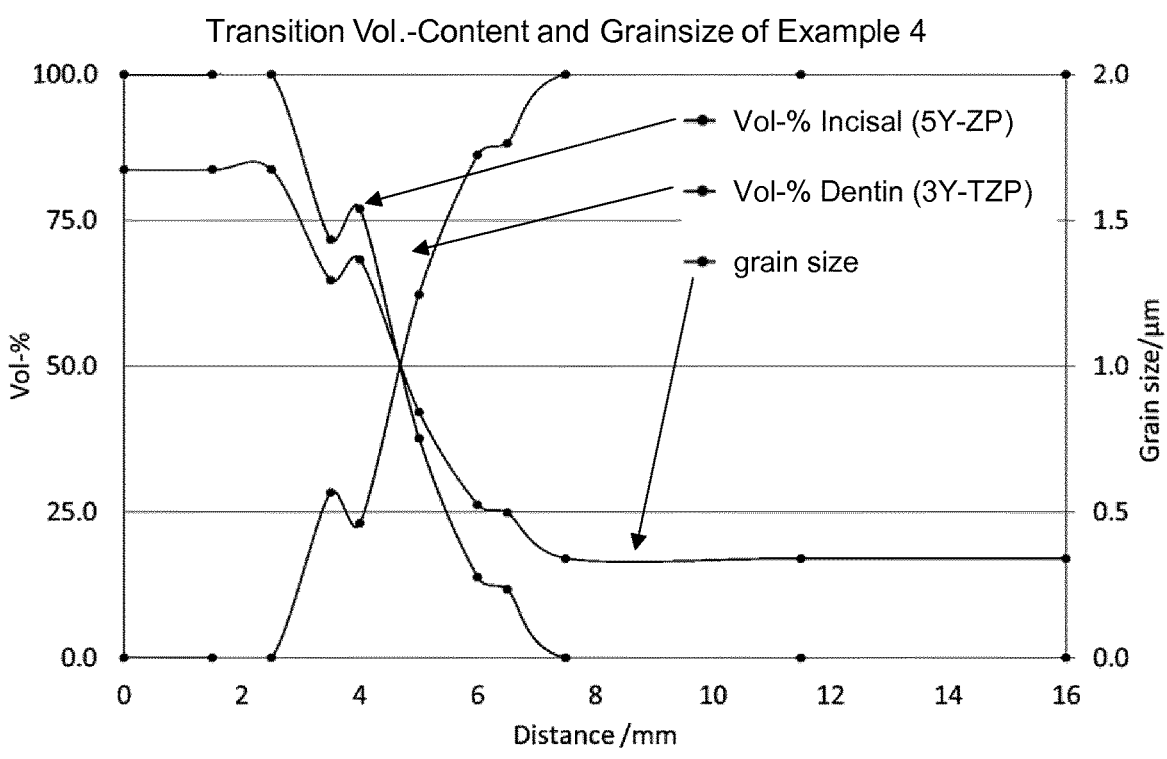
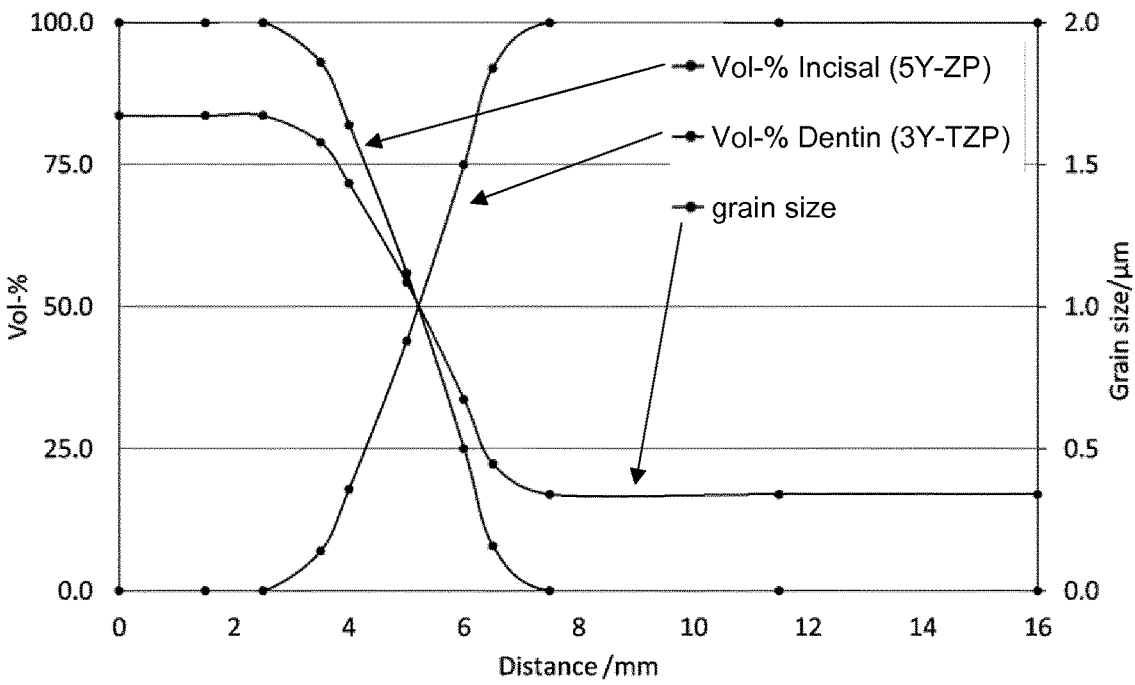
Figure 11

| | | C | a | b |
|---|---|---|---|---|
| | 1 | 100 | 1 | -1.3 |
| exp | 2 | 100 | 1 | -3 |
| | 3 | 100 | 1 | -1 |

$$P(t) = \frac{c}{1 + a \cdot e^{-b \cdot t}}$$

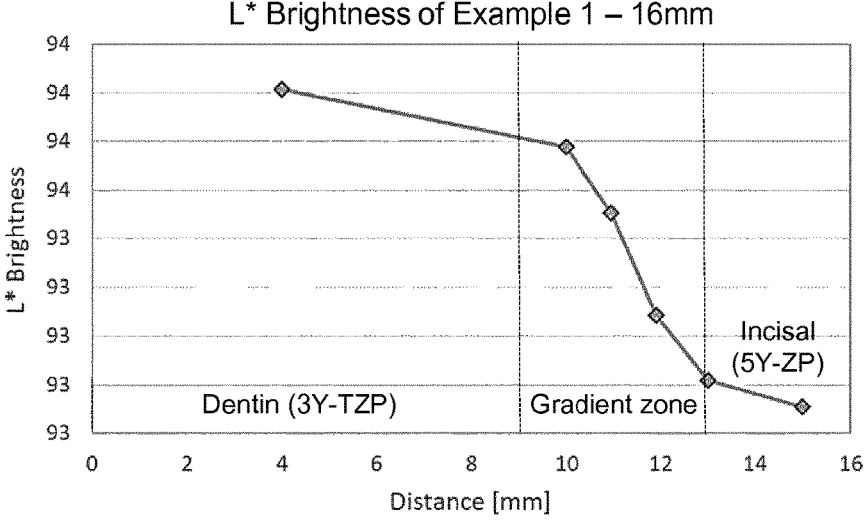
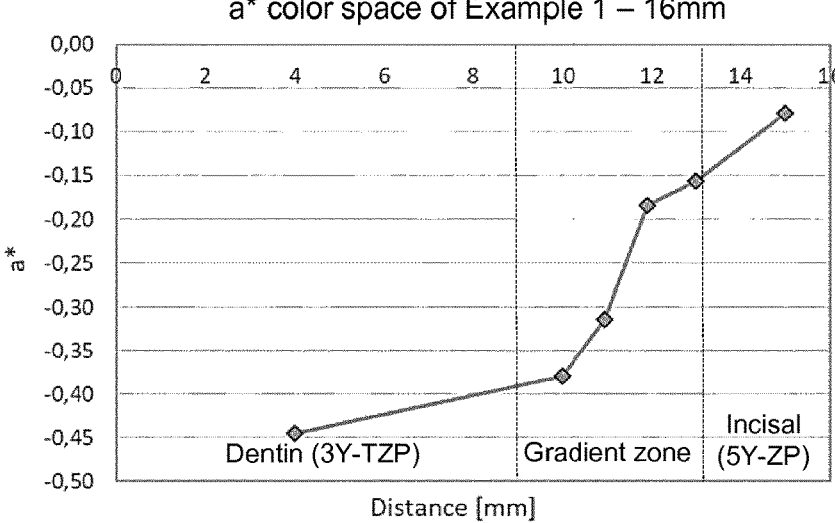
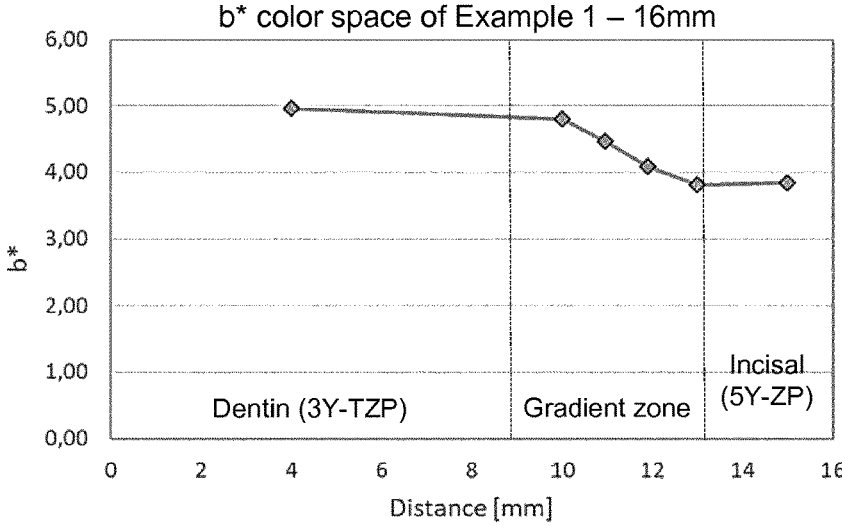
Figure 16

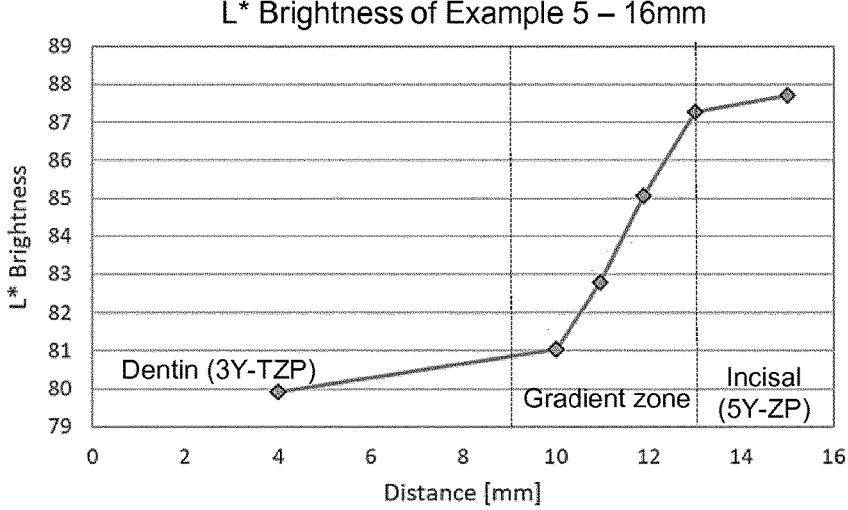
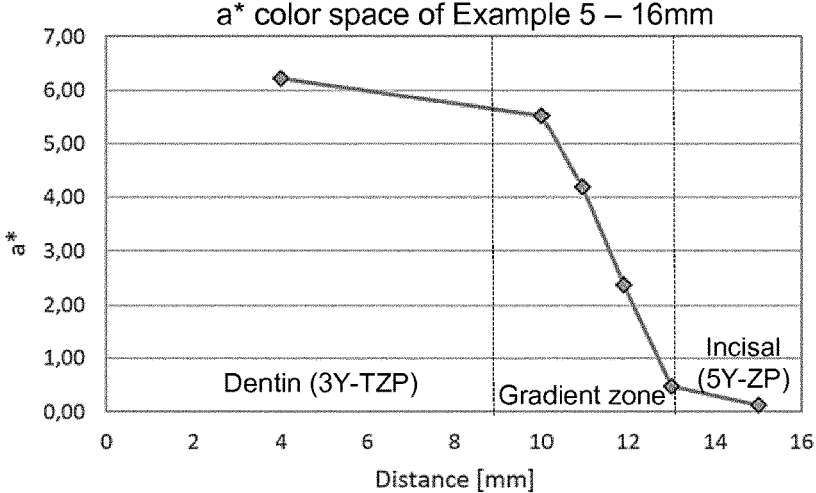
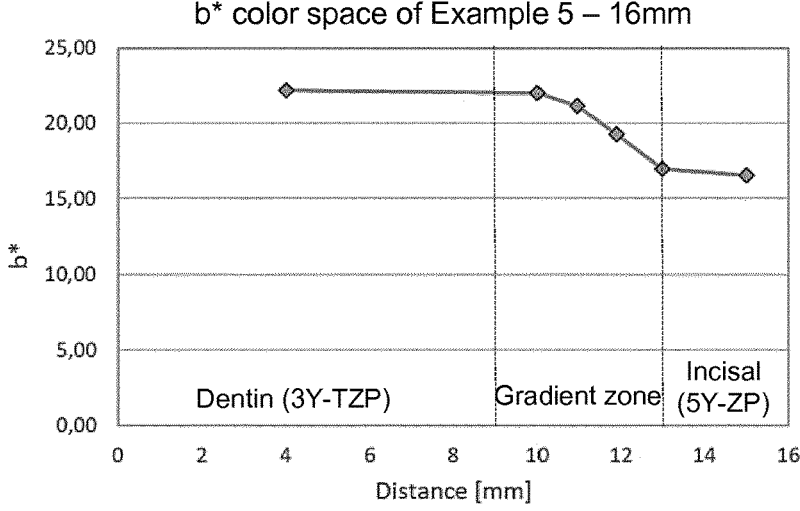
Figure 18

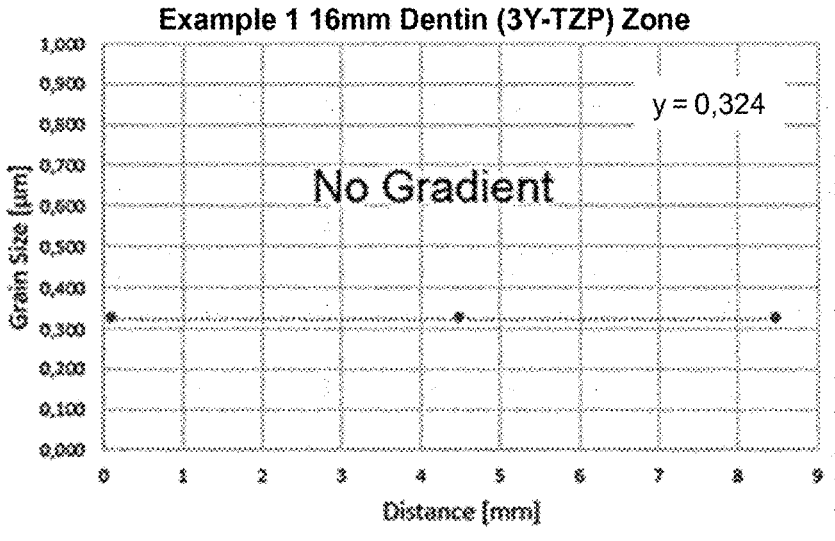
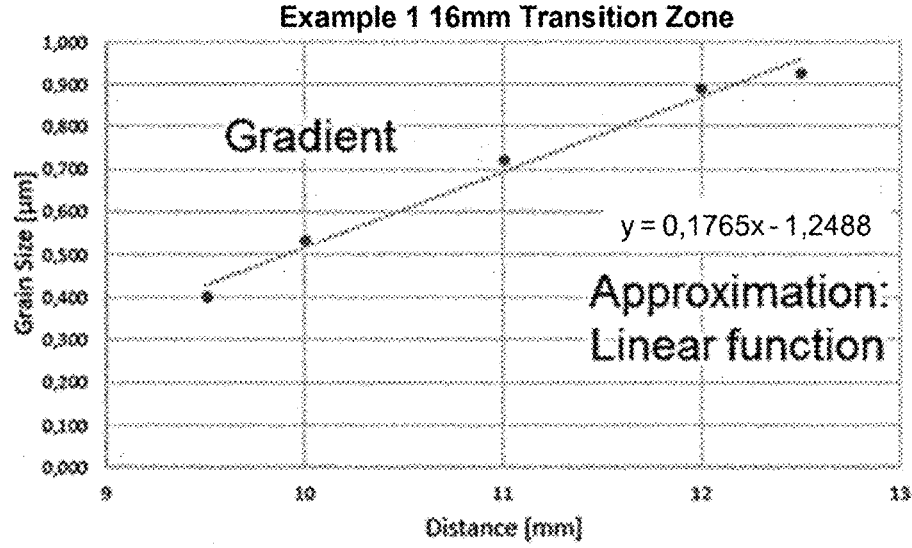
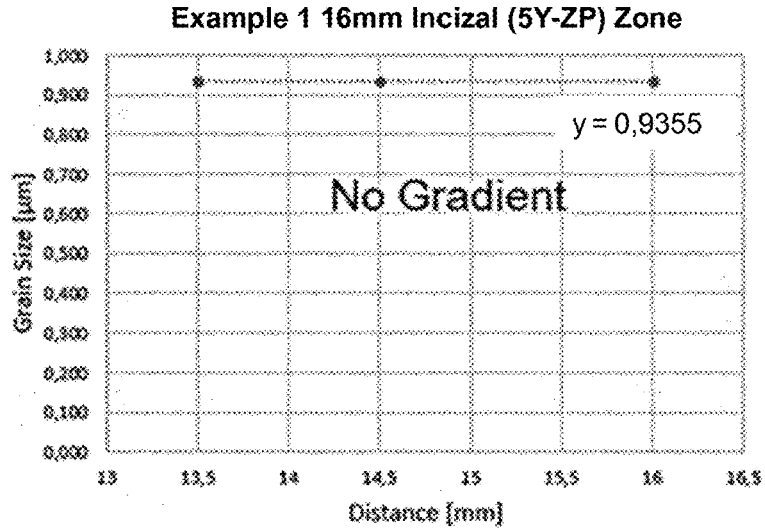
Figure 21

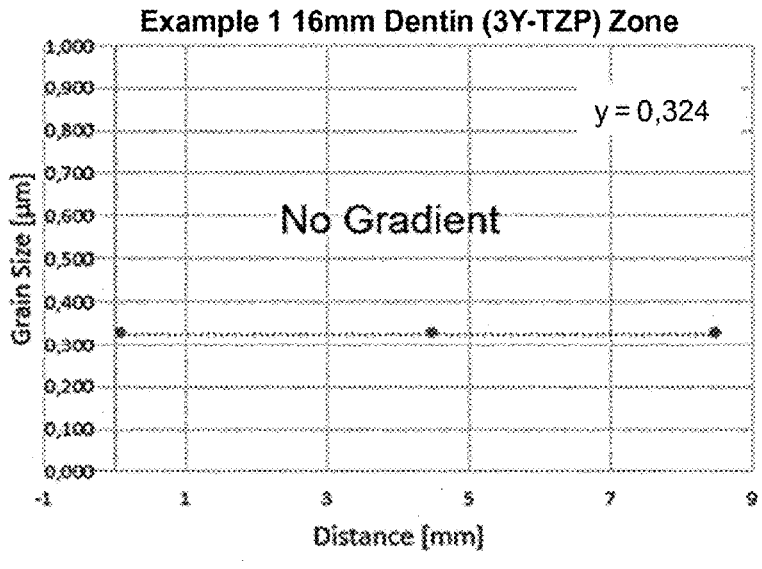
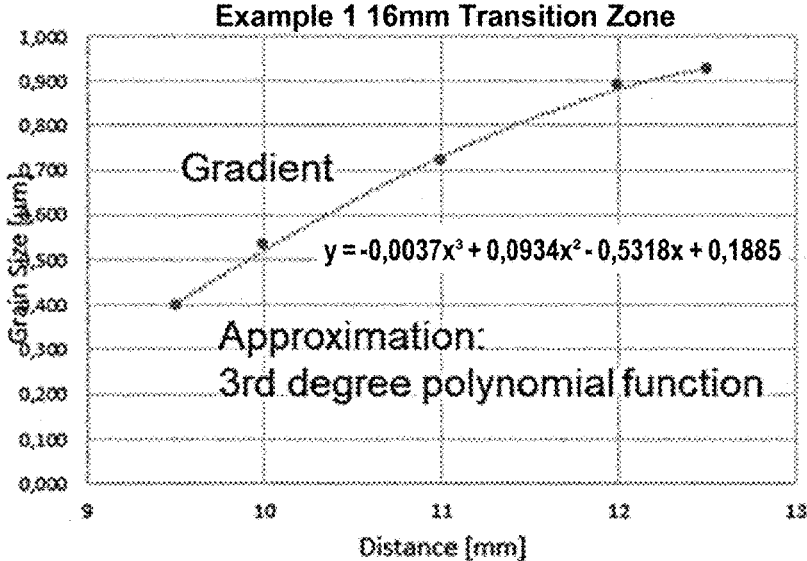
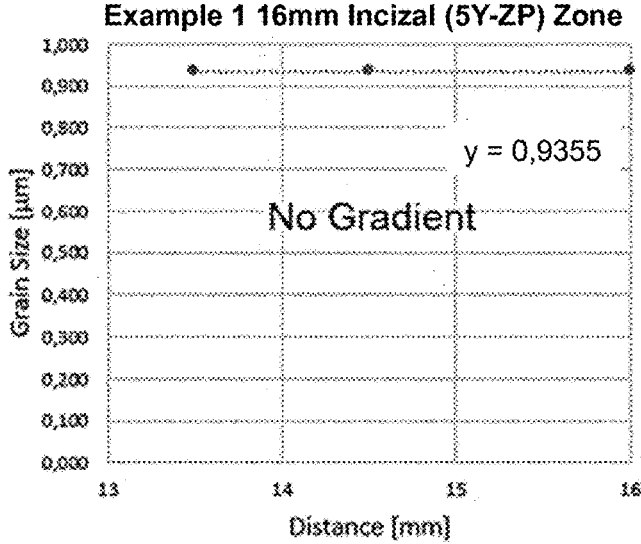
Figure 22

Type I
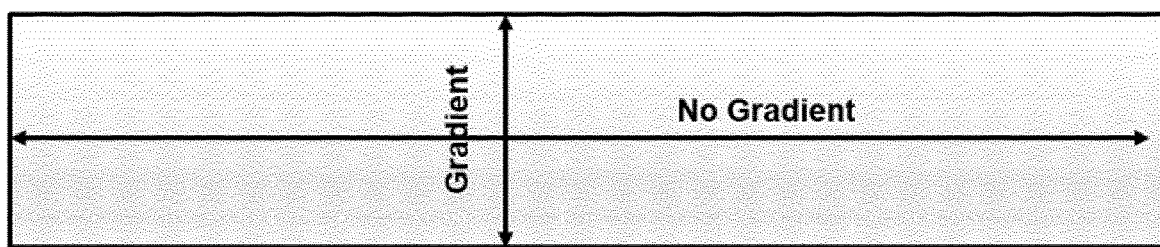
Type II
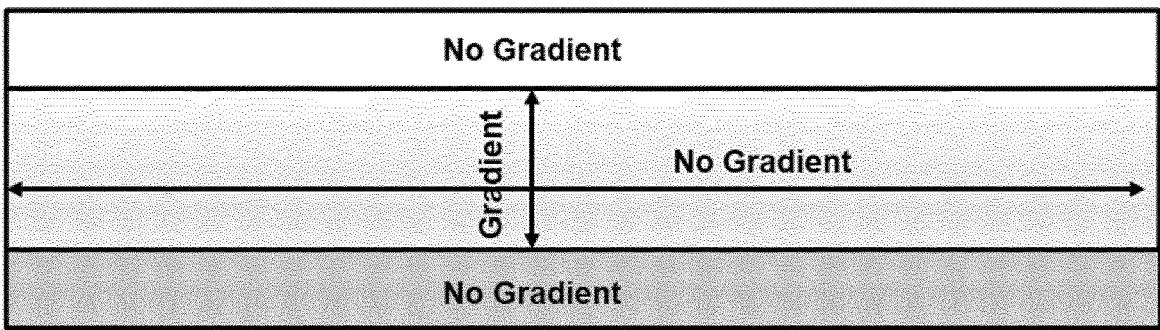
Type III
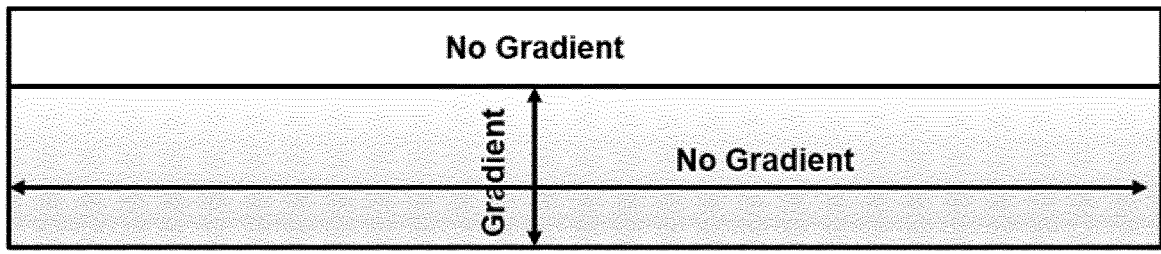
Type IV
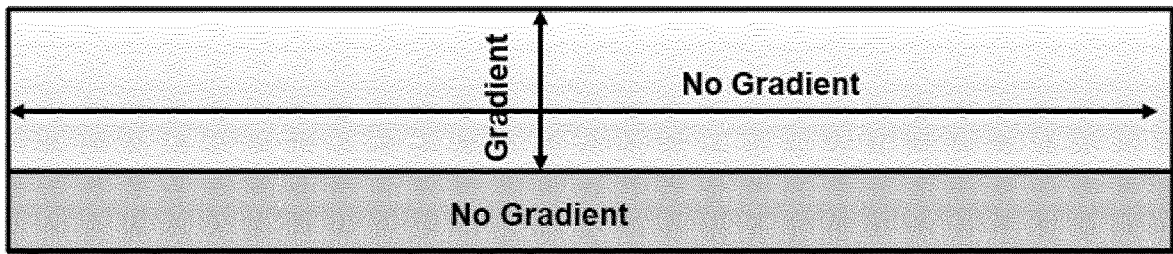
Figure 23

Type V
Gradient 1 ≠ Gradient 2 (linear, non-linear or combination thereof)
Type VI
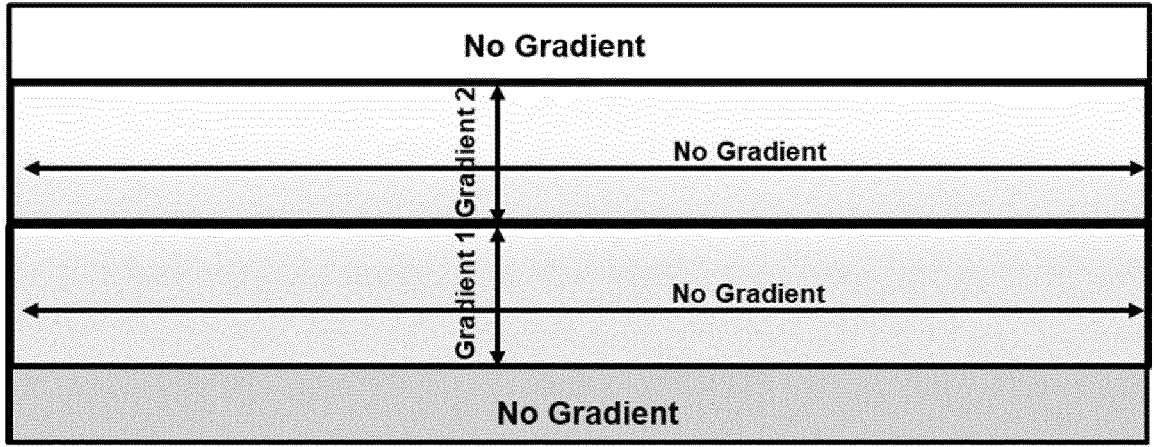
Gradient 1 ≠ Gradient 2 (linear, non-linear or combination thereof)
Figure 23 (cont.)

Type VII

Gradient 1 ≠ Gradient 2 (linear, non-linear or combination thereof)

Type VIII

Gradient 1 ≠ Gradient 2 (linear, non-linear or combination thereof)

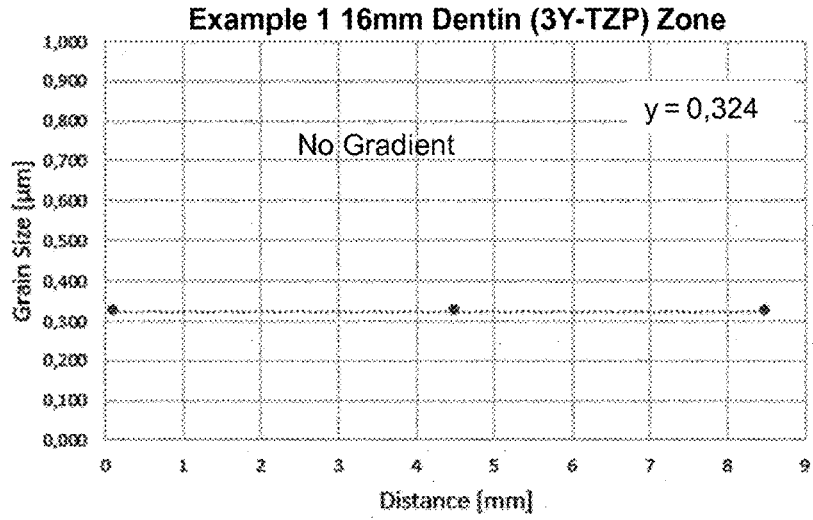
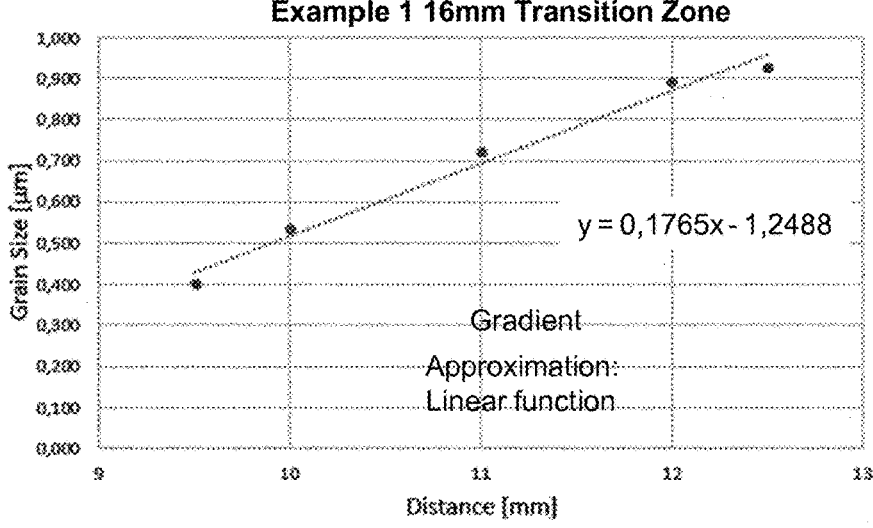
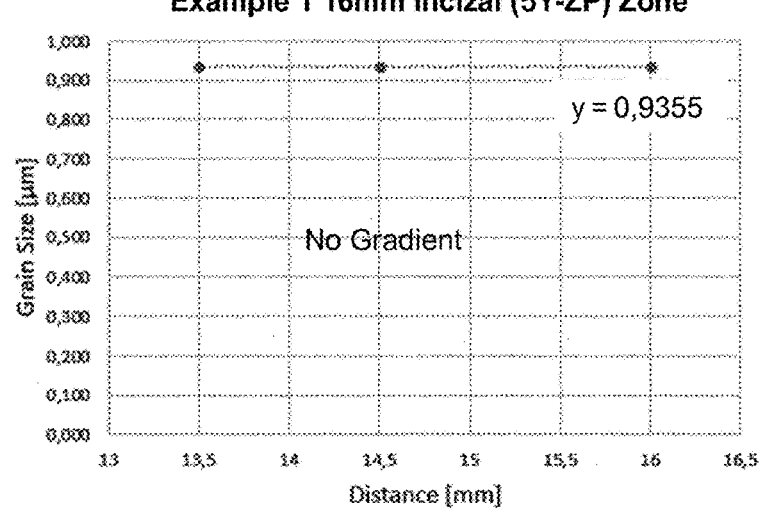
Figure 26

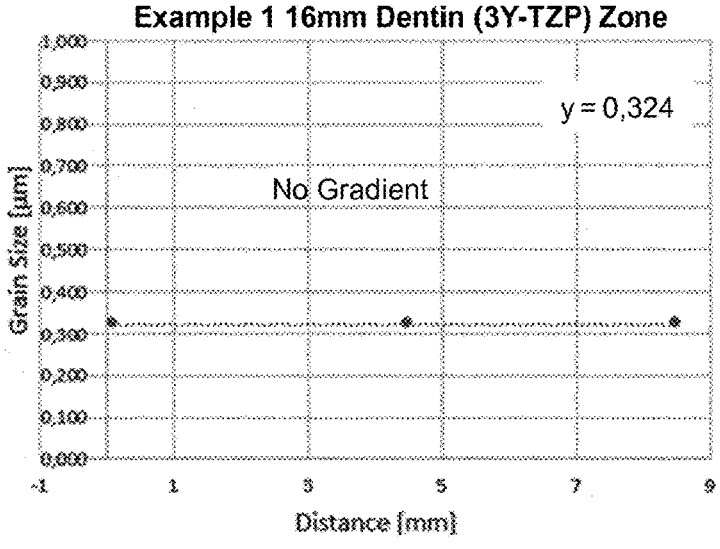
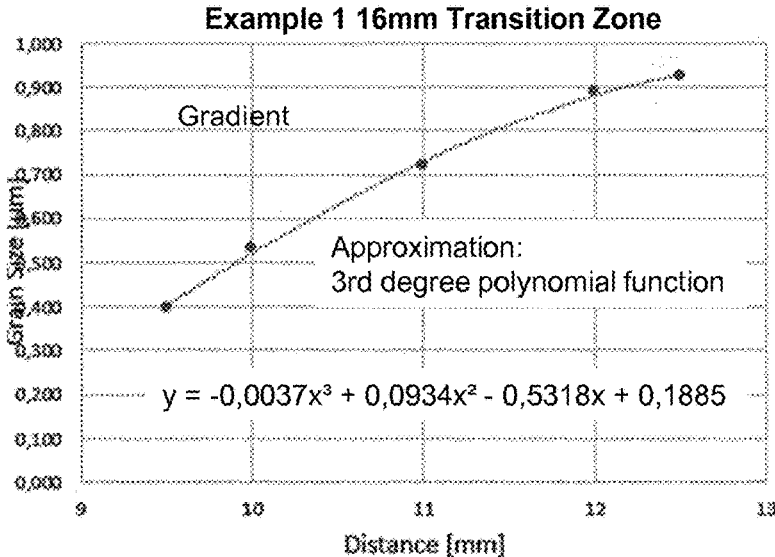
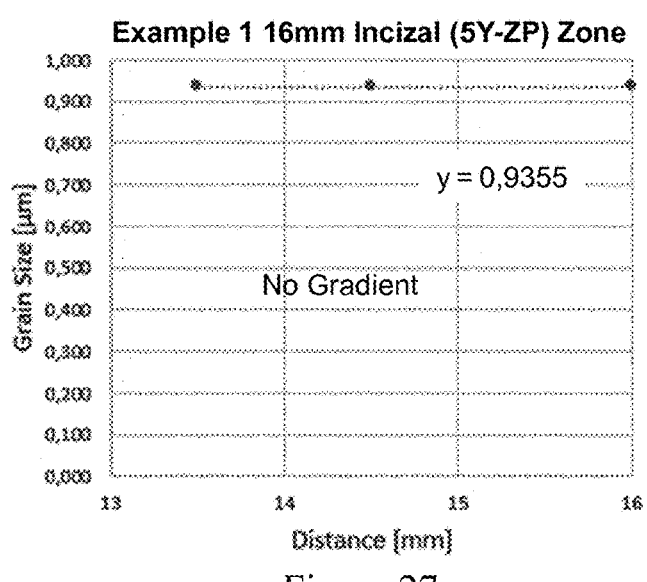
Figure 27

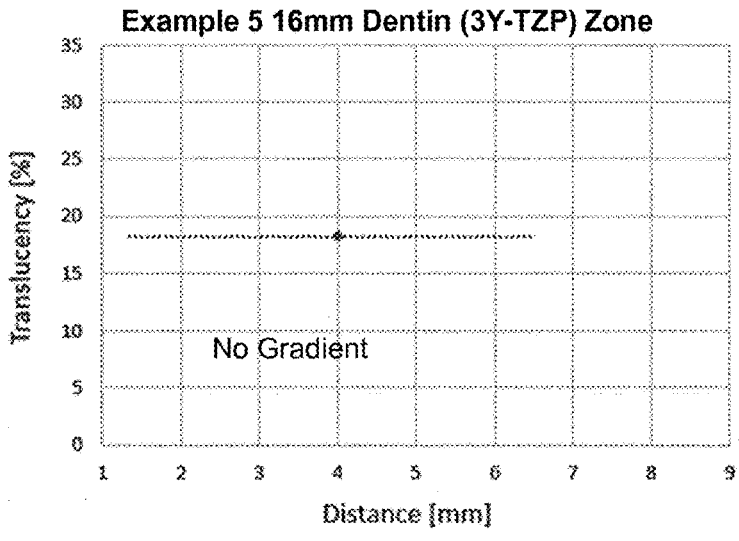
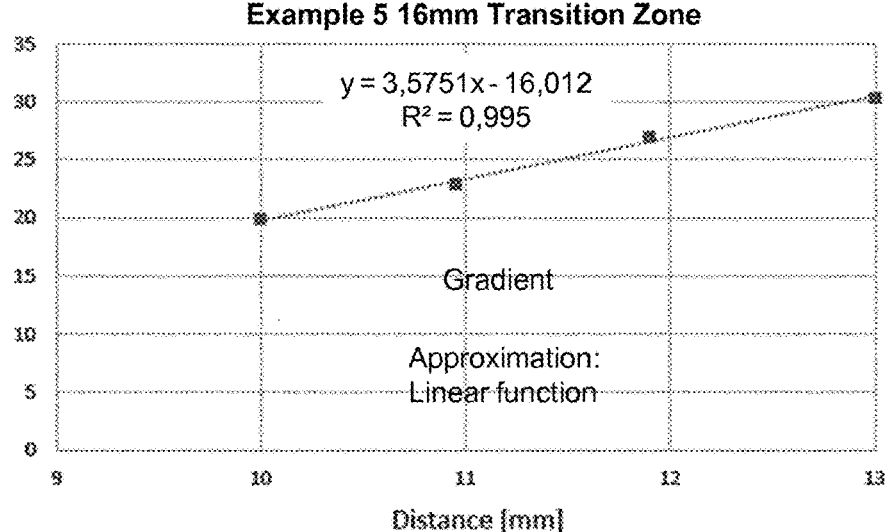
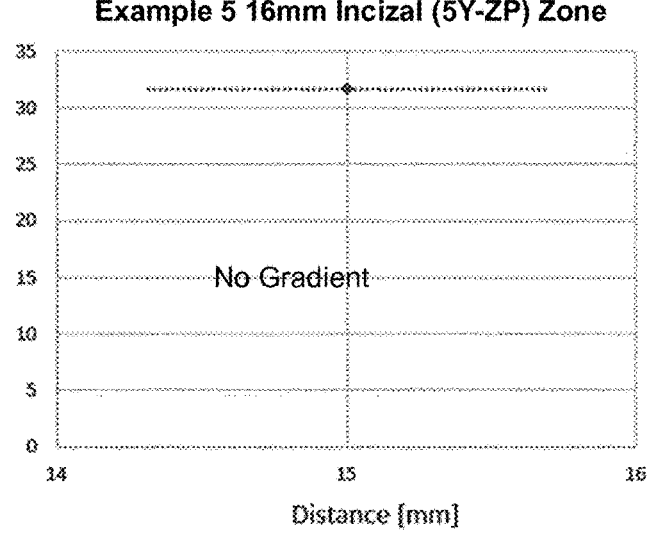
Figure 28

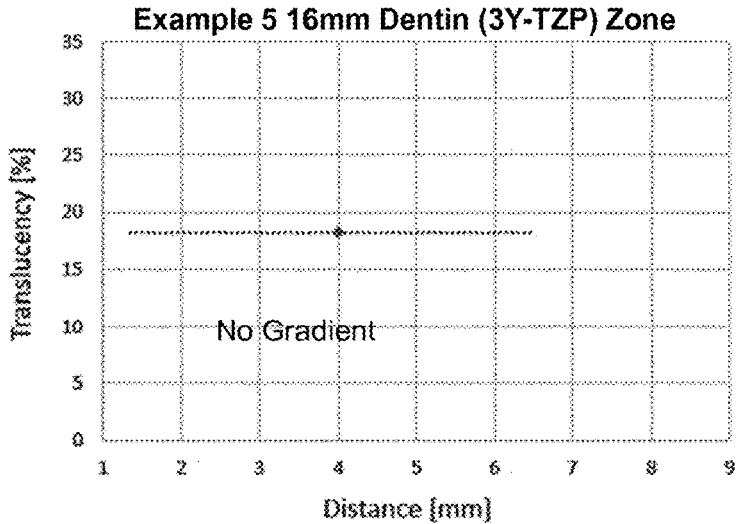
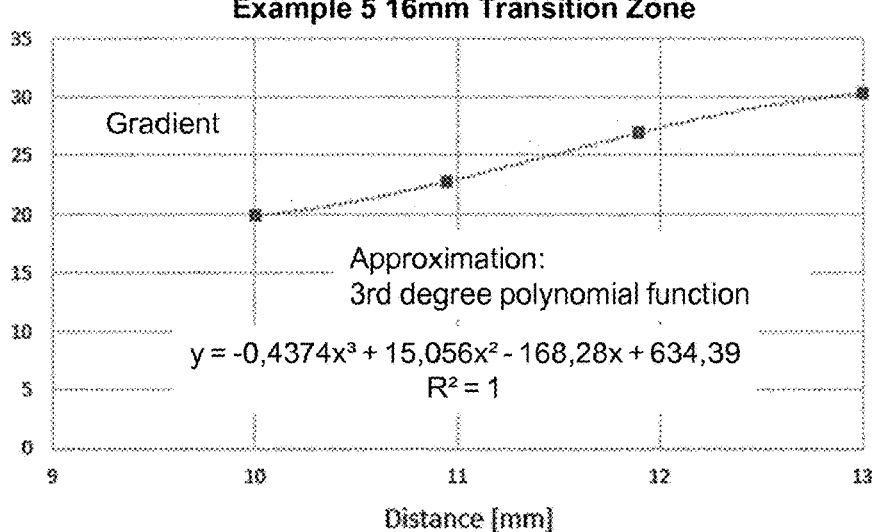
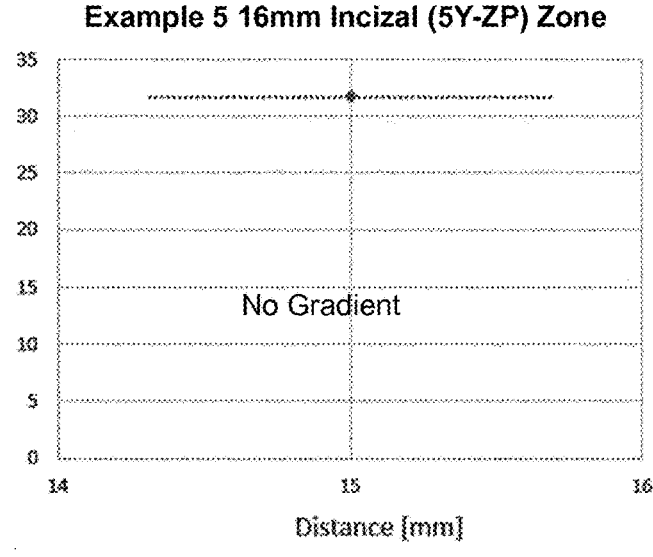
Figure 29

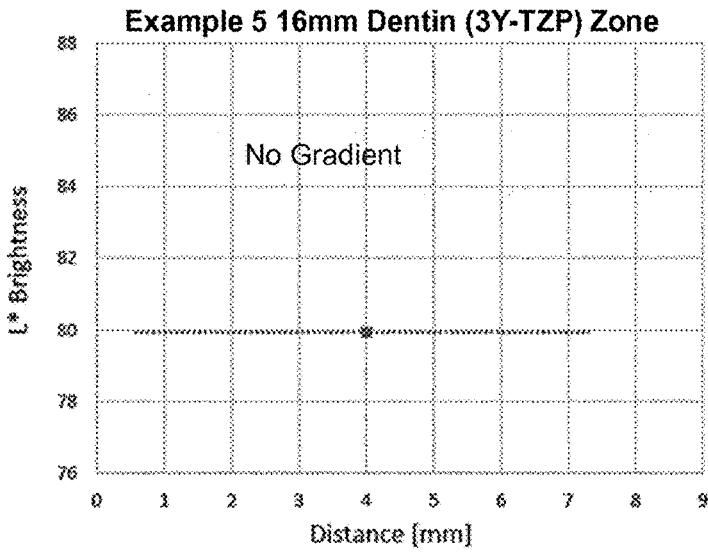
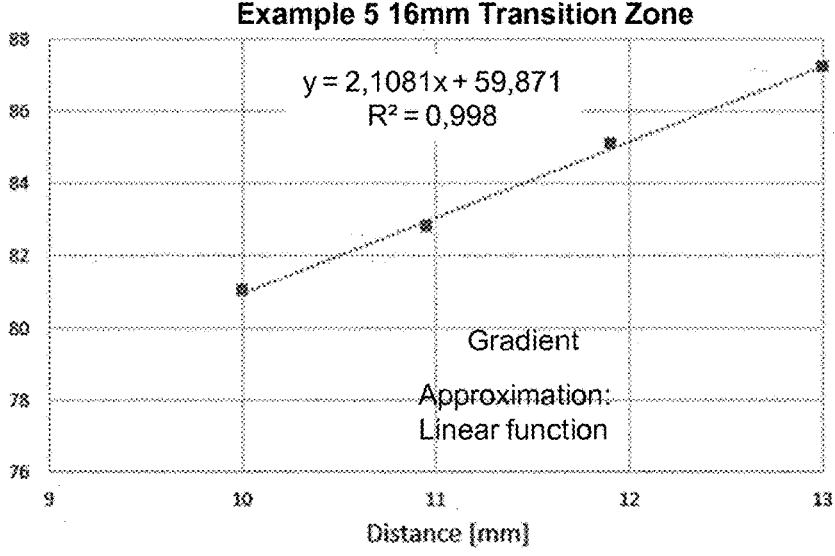
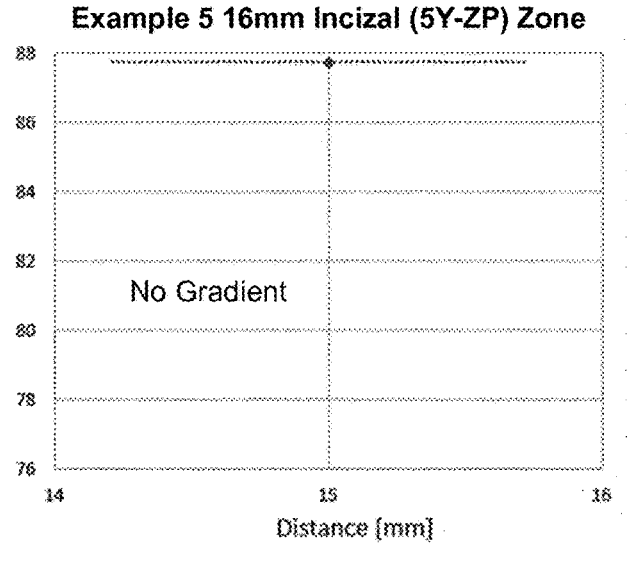
Figure 30

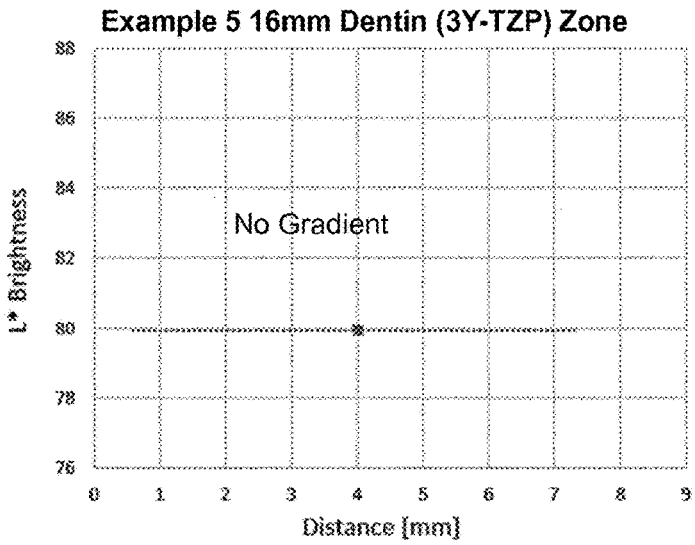
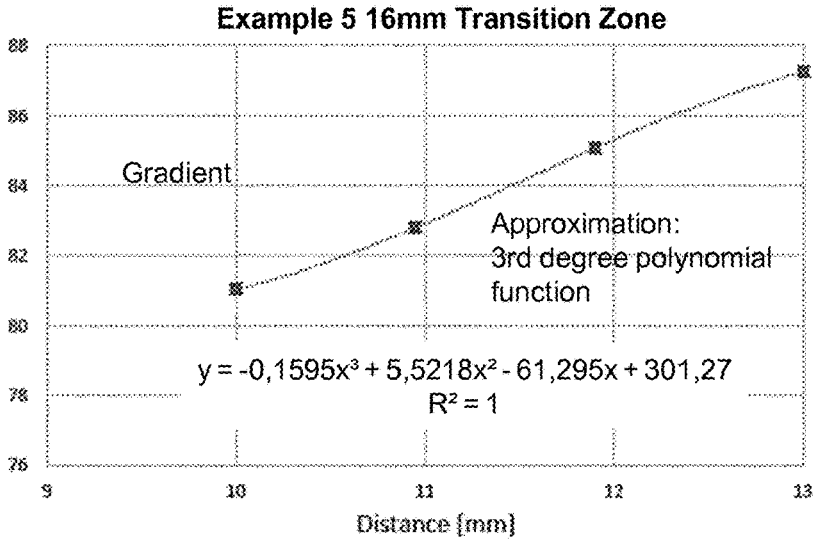
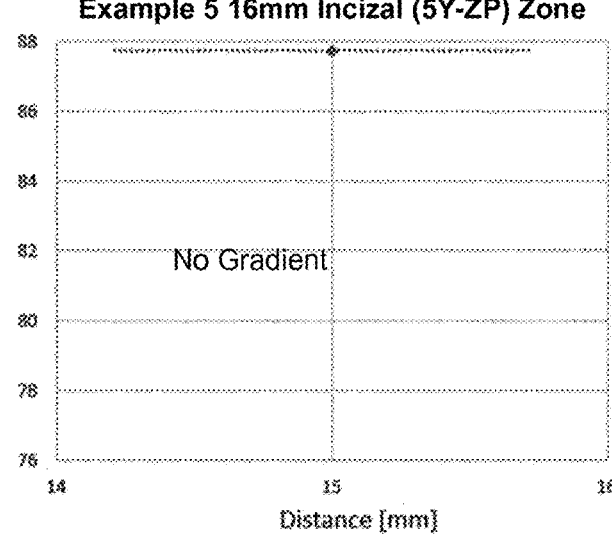
Figure 31

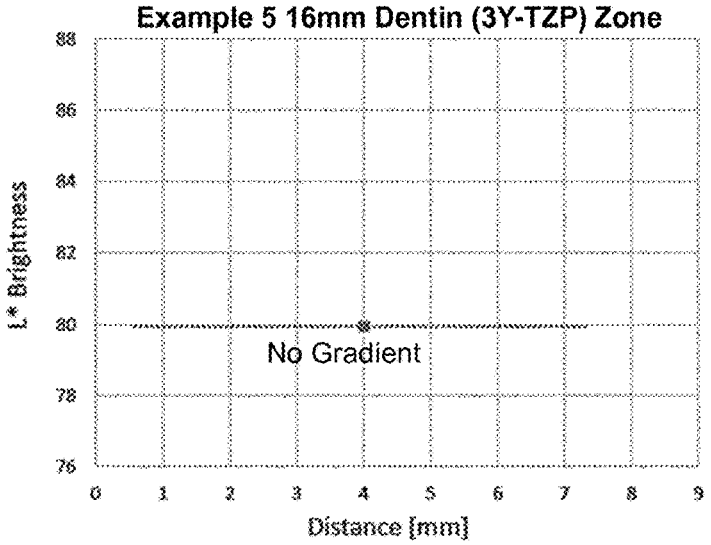
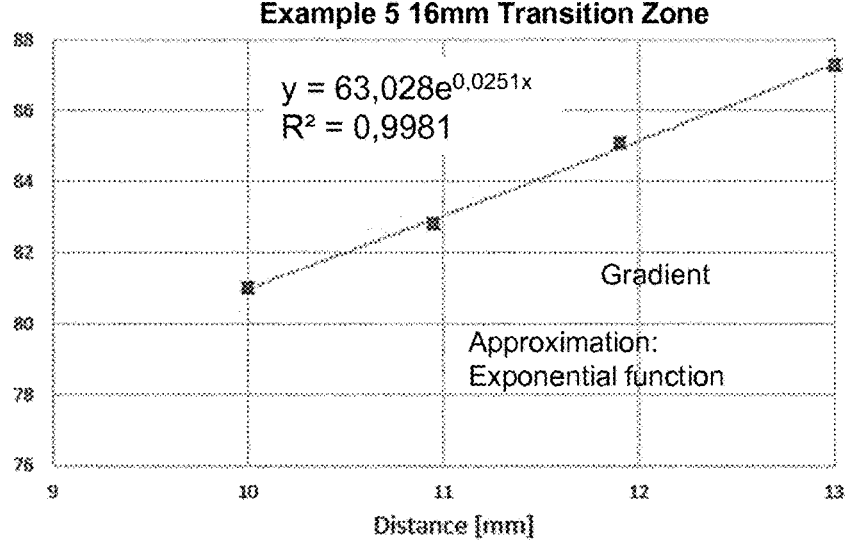
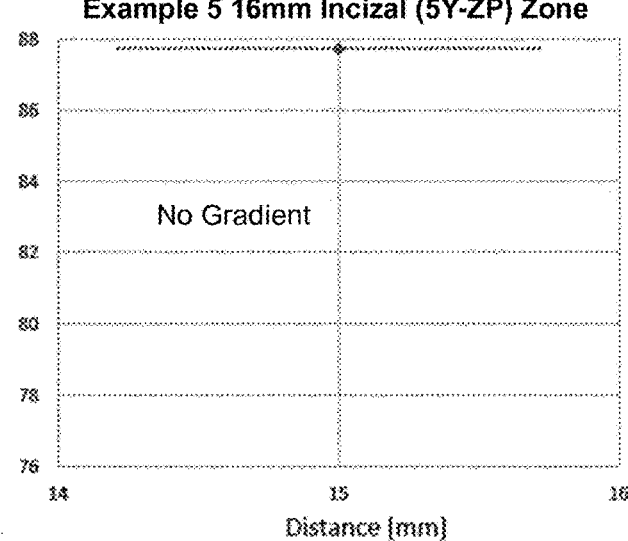
Figure 32

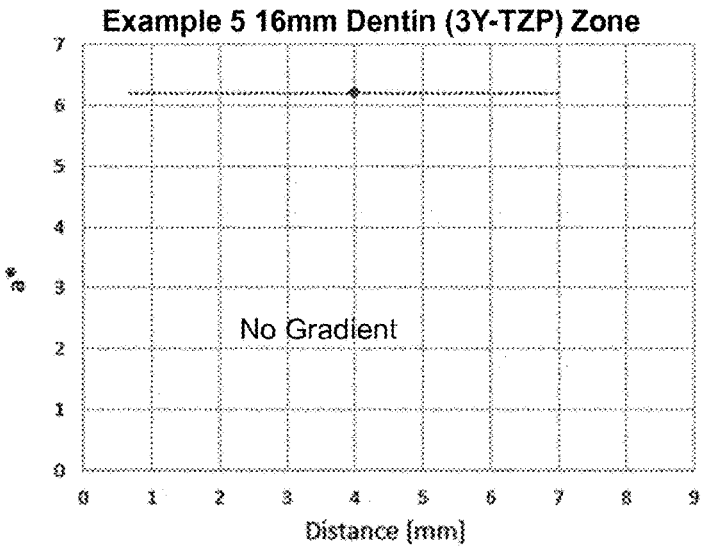
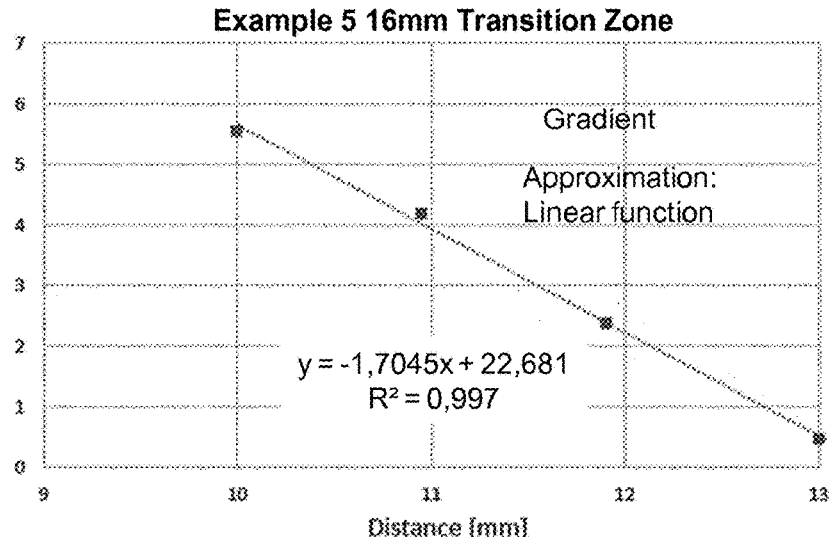
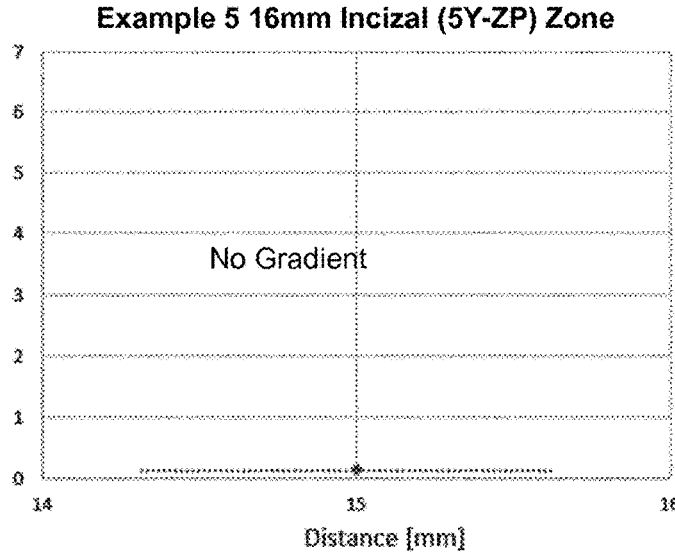
Figure 33

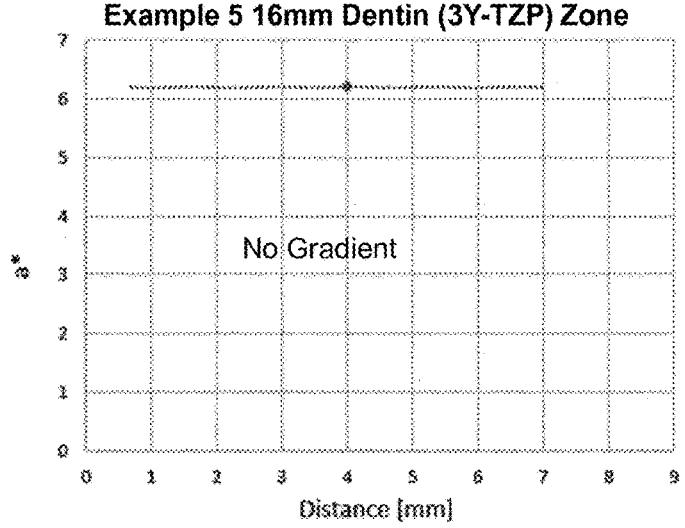
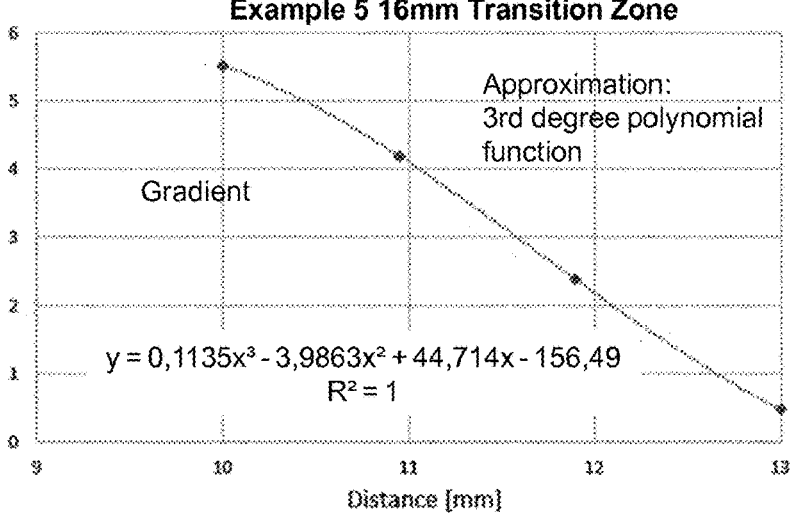
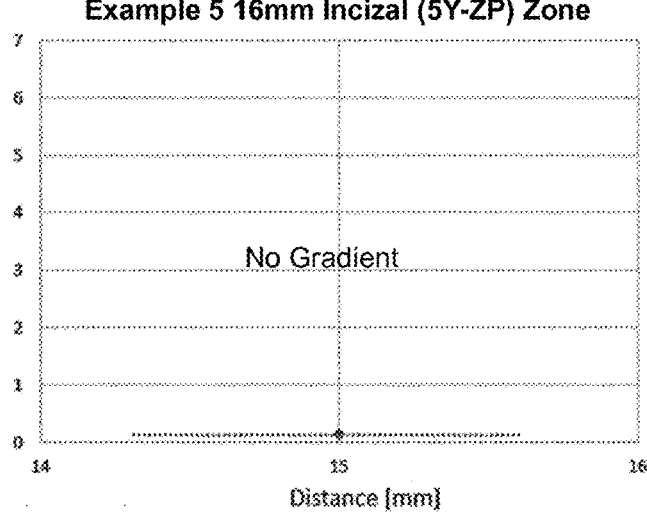
Figure 34

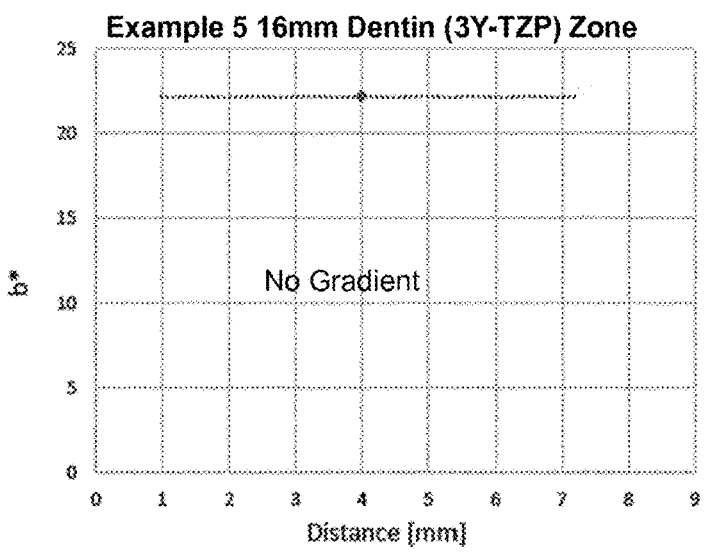
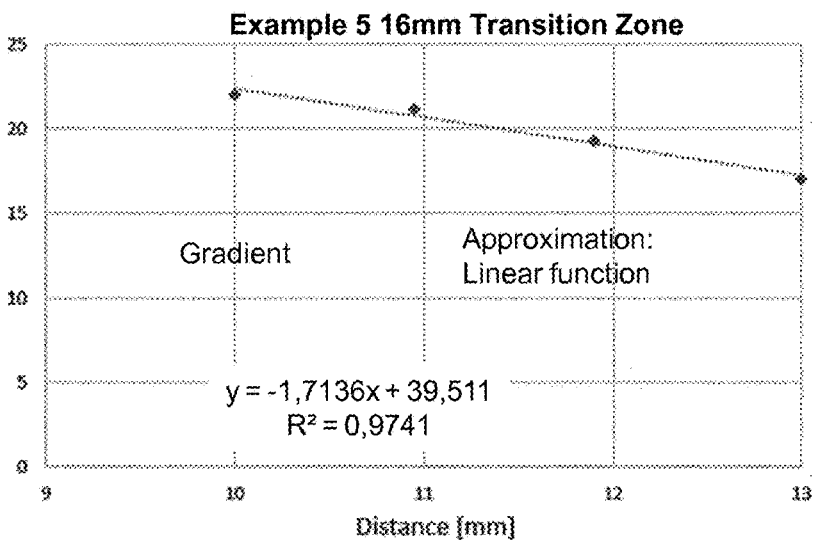
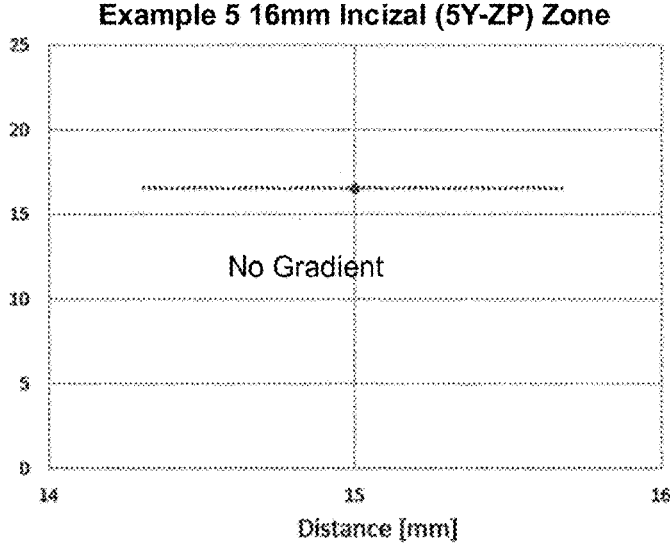
Figure 35

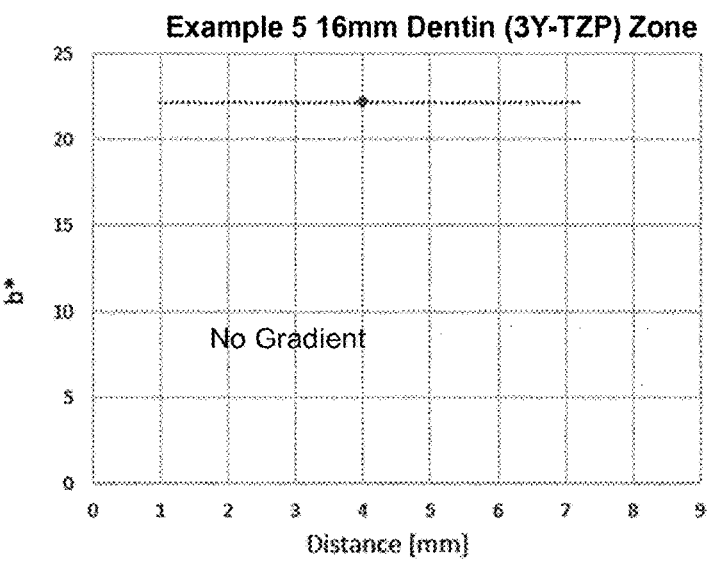
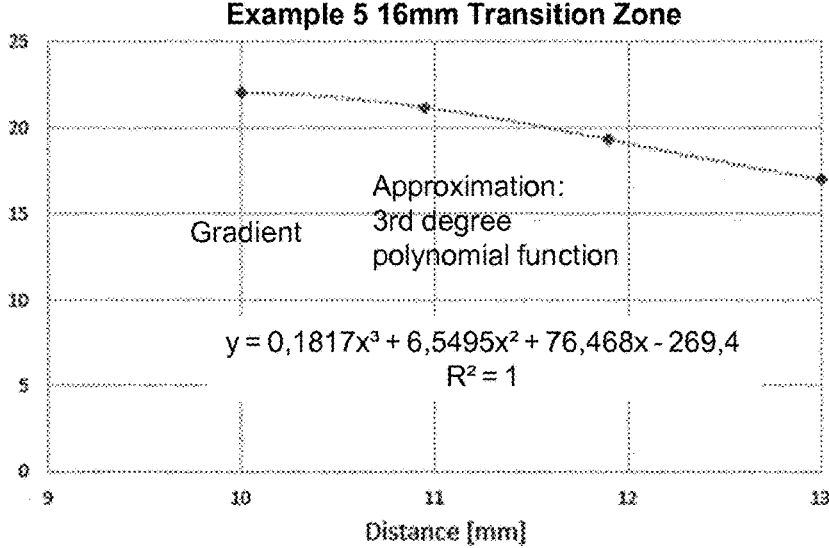
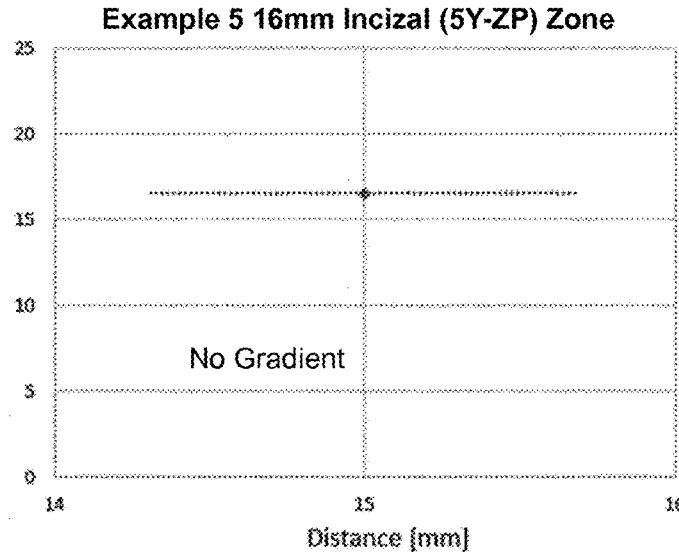
Figure 36

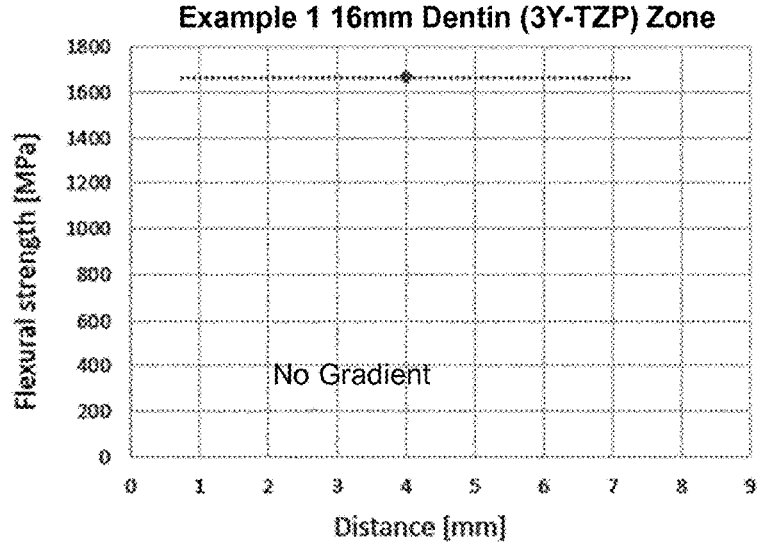
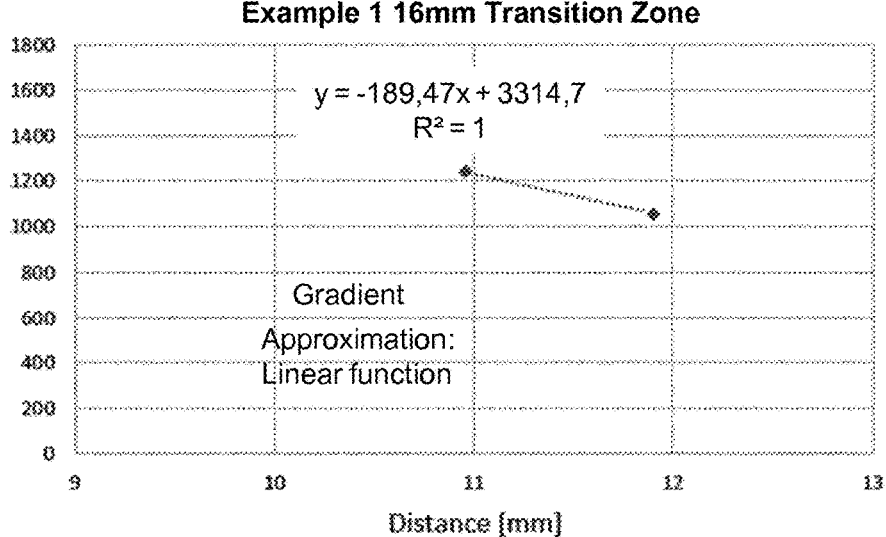
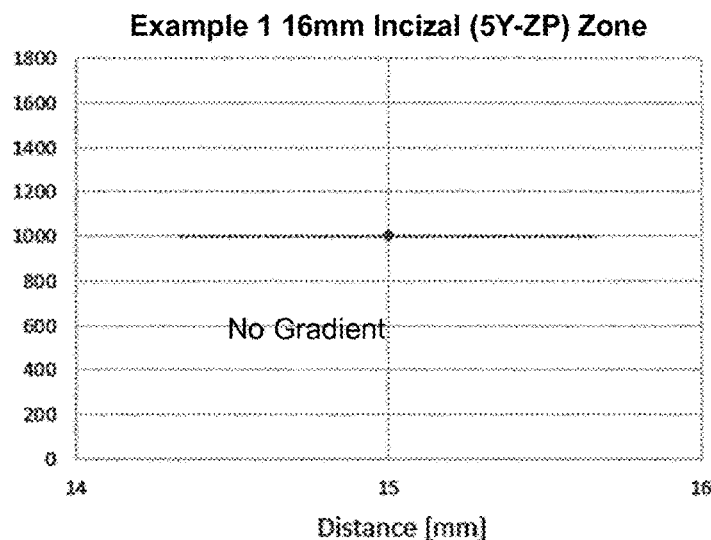
Figure 37

GRADIENT COMPOSITION ZIRCONIA DENTAL MATERIALS

BACKGROUND OF THE DISCLOSURE

Ceramics such as zirconia-based materials have emerged as high-strength dental materials for dental restorations/prostheses. A finished dental restoration should match the color of the patient's teeth, i.e., it should be "tooth colored." The colors of human teeth appear to range from a light almost white-tan to a light brown, and occupy a very specific color space. This color space can be described by the commonly used CIE (Commission Internationale de l'Eclariage) L*, a*, b* conventions.

However, zirconia-based materials, in particular uncolored zirconia-based materials, are often an intense white color and have low translucency, and consequently the esthetics of the finished restoration/prosthesis looks like an unnatural tooth and is undesirable in terms of its color. Layered zirconia materials have emerged to improve the esthetics of this material, but even state-of-the-art layered zirconia materials, where the layers have different colors and/or translucency, still cannot compare with the esthetics of natural teeth. Layered zirconia materials have discrete layers and have a demarcation between the layers where there is a change in color and/or translucency, and this is one reason these layered materials do not replicate the esthetics of natural teeth.

Based on at least the foregoing, there exists and ongoing an unmet need in the art for improved zirconia-based materials for dental applications.

SUMMARY OF THE DISCLOSURE

The present disclosure provides pre-sintered zirconia dental ceramic materials, sintered zirconia dental ceramic materials, and dental articles. The present disclosure also provides methods of making the pre-sintered dental zirconia dental ceramic materials and the sintered ceramic materials. The present disclosure provides, in various examples, sintered zirconia dental materials and dental articles that exhibit a smooth gradient transition of translucency and color between dentin to incisal regions of the materials/articles to replicate natural dentition, while still maintaining the desirable biaxial flexural strength typically associated with high-strength zirconia. The present disclosure provides this smooth gradient transition or color and/or translucency, without discrete layers, between the incisal and dentin regions or zones, by utilizing a transition or gradient zone between the incisal and dentin zones. The present disclosure further provides, in various examples, no observable layers or demarcation in the translucency and/or color within the gradient zone, or transition between the incisal, gradient and dentin regions or zones. Observable means by visual inspection or optical microscopy (e.g., observable using a microscope at a magnification of 30×, 25×, 20×, 15×, 10×, 5×, 2× or by the naked eye). A smooth transition refers to this lack of observable layers or demarcation within the gradient zone, or transition between the incisal, gradient and dentin regions or zones. The present disclosure further provides, in various examples, sintered zirconia dental materials and dental articles that exhibit a incisal zone that is a constant translucency and/or color that transitions into a gradient zone with a smooth transition, the gradient zone includes a smooth gradient (no observable demarcation or layers) of translucency and/or color, which smoothly transitions into dentin zone that has a constant translucency and/or color.

The present disclosure further provides, in various examples a sintered zirconia dental materials and dental articles that have different but constant yttria content in the incisal and dentin zones exhibiting constant translucency and/or color, with a gradient zone between the incisal and dentin zone that has a yttria content gradient.

In an aspect, the present disclosure provides pre-sintered zirconia dental ceramic materials and sintered zirconia dental ceramic materials. The pre-sintered zirconia dental ceramic materials comprise yttria and the pre-sintered zirconia dental ceramic materials have a yttria content gradient. A pre-sintered zirconia dental ceramic material can be sintered to form at least partially or fully sintered material, which may be a dental article. Without intending to be bound by any particular theory, it is considered that the sintered zirconia dental ceramic materials of the present disclosure exhibit color or translucency gradient or color and translucency gradient resulting in esthetics similar to or of a natural tooth, without the use of a layered material. A pre-sintered zirconia dental ceramic material has a gradient in yttria content in at least a portion or all of the pre-sintered zirconia dental ceramic material. A gradient in yttria content may be referred to as a gradient in yttria concentration. The gradient may be a continuous and uninterrupted gradient. The gradient may be a linear or non-linear gradient. The gradient may be in a direction normal to a longest dimension of the pre-sintered zirconia dental ceramic material. A pre-sintered zirconia dental ceramic material may have different zones, which may be incisal zone(s), dentin zone(s), or transition zone(s). Transition zone(s) may be referred to herein as gradient zone(s). The pre-sintered zirconia dental ceramic materials can have various form factors (e.g., shapes and/or sizes).

In an aspect, the present disclosure provides methods of making pre-sintered zirconia dental ceramic materials. Pre-sintered zirconia dental ceramic materials of the present disclosure can be made by a method of the present disclosure. In various examples, a pre-sintered zirconia dental ceramic material is made by a method of the present disclosure. In various examples, a method of making a pre-sintered zirconia dental ceramic material having a gradient yttria content in at least a portion or all of the pre-sintered zirconia dental ceramic material comprises: forming a monolithic structure (e.g., a green structure) from at least a first zirconia ceramic powder having a first yttria content and a second zirconia ceramic powder having a second yttria content, wherein the first yttria content is different than the second yttria content; subjecting the monolithic structure to uniaxial pressing (e.g., to form a green compact structure); subjecting the uniaxially pressed monolithic structure to cold isotactic; and heating (e.g., presintering) the uniaxial pressed and cold isostatic pressed monolithic structure, where a pre-sintered zirconia dental ceramic material is formed. A monolithic structure or resulting pre-sintered zirconia dental material may comprise a plurality of zones (e.g., incisal zone(s), transition zone(s), and dentin zone(s)). A transition zone may have a linear or non-linear gradient in yttria content. A monolithic structure may be formed by mixing two or more zirconia ceramic powders having one or more different yttria content. The pre-sintered zirconia dental ceramic may be sintered to form a sintered (e.g., partially sintered or fully/dense sintered) zirconia dental ceramic.

In an aspect, the present disclosure provides sintered zirconia dental ceramic materials. Sintered zirconia dental ceramic material of the present disclosure can be made by a method of the present disclosure. A sintered zirconia material can have the same composition (e.g., elemental composition) as described herein for pre-sintered materials. A sintered zirconia dental ceramic material may be a partially sintered or fully sintered zirconia dental ceramic material. A sintered zirconia dental ceramic may comprise a plurality of zones (e.g., incisal zone(s), transition zone(s), and dentin zone(s)). The zones may correspond to the zones of the monolith and/or pre-sintered zirconia dental materials from which the sintered zirconia dental material is made. A zone may have different composition and/or one or more different properties (e.g., physical/mechanical property(ies), which include, but are not limited to biaxial flexural strength, fracture toughness, and the like, optical property(ies), which include, but are not limited to, color, shade, L*, a*, b* values, translucency, and the like), or a combination thereof) that one or more of the other zones.

In an aspect, the present disclosure provides dental articles. A dental article of the present disclosure may be made by a method of the present disclosure. In various examples, a dental article is made using a pre-sintered zirconia dental ceramic material of the present disclosure. In various examples, a dental article comprises (or is formed of) sintered zirconia dental ceramic material of the present disclosure. A dental article may have various form factors. In various examples, the dental article is a blank or smart blank. In various other examples, the dental article is a dental restoration. A dental article may have (e.g., exhibit) one or more desirable physical/mechanical and/or one or more desirable optical property. The desirable physical/mechanical and/or one or more desirable optical property are as described herein for the sintered zirconia dental ceramic material.

BRIEF DESCRIPTION OF THE FIGURES

For a fuller understanding of the nature and objects of the disclosure, reference should be made to the following detailed description taken in conjunction with the accompanying figures.

FIG. 7 shows the properties of examples of a pre-sintered body.

FIG. 8 shows the properties of an example of a sintered body.

FIG. 9 shows grain size and powder distribution of Example 1 (disc height 16 mm).

FIG. 10 shows grain size and powder distribution of Example 3 (disc height 16 mm).

FIG. 11 shows grain size and powder distribution of Example 4 (disc height 16 mm).

FIG. 16 shows a color gradient for Example 1 (disc height 16 mm). Color space is L*a*b*. Thickness of samples is 1.0 mm.

FIG. 18 shows a color gradient for Example 5 (disc height 16 mm). Color space is L*a*b*. Thickness of samples is 1.0 mm.

FIG. 21 shows grain size as a function of distance (disc height is 16 mm) using a linear function.

FIG. 22 shows grain size as a function of distance (disc height is 16 mm) using a linear function.

FIG. 26 shows an example of grain size as a function of distance (disc height 16 mm) and an example of a linear gradient function.

FIG. 27 shows an example of grain size as a function of distance (disc height 16 mm) and an example of a $3^{rd}$ degree polynomial gradient function.

FIG. 28 shows an example of translucency as a function of distance (disc height 16 mm) and example of a linear gradient function. Only one data point was measured for the dentin zone because the chemical composition within this zone is the same. It can be assumed that more measurements within the dentin zone provide identical values. The same also applies for the incisal zone.

FIG. 29 shows an example of translucency as a function of distance (disc height 16 mm) and an example of a 3rd degree polynomial gradient function.

FIG. 30 shows an example of L* brightness as a function of distance (disc height 16 mm) and an example of a linear gradient function.

FIG. 31 shows and example of L* brightness as a function of distance (disc height 16 mm) and an example of a 3rd degree polynomial gradient function.

FIG. 32 shows and example of L* brightness as a function of distance (disc height 16 mm) and an example of an exponential function.

FIG. 33 shows an example of a* values as a function of distance (disc height 16 mm) and an example of a linear gradient function.

FIG. 34 shows an example of a* values as a function of distance (disc height 16 mm) and an example of a 3rd degree polynomial gradient function.

FIG. 35 shows an example of b* values as a function of distance (disc height 16 mm) and an example of a linear gradient function.

FIG. 36 shows an example of b* values as a function of distance (disc height 16 mm) and an example of a 3rd degree polynomial gradient function.

FIG. 37 shows an example of biaxial flexural strength as a function of distance (disc height 16 mm) and an example of a linear gradient function.

Figure 38:
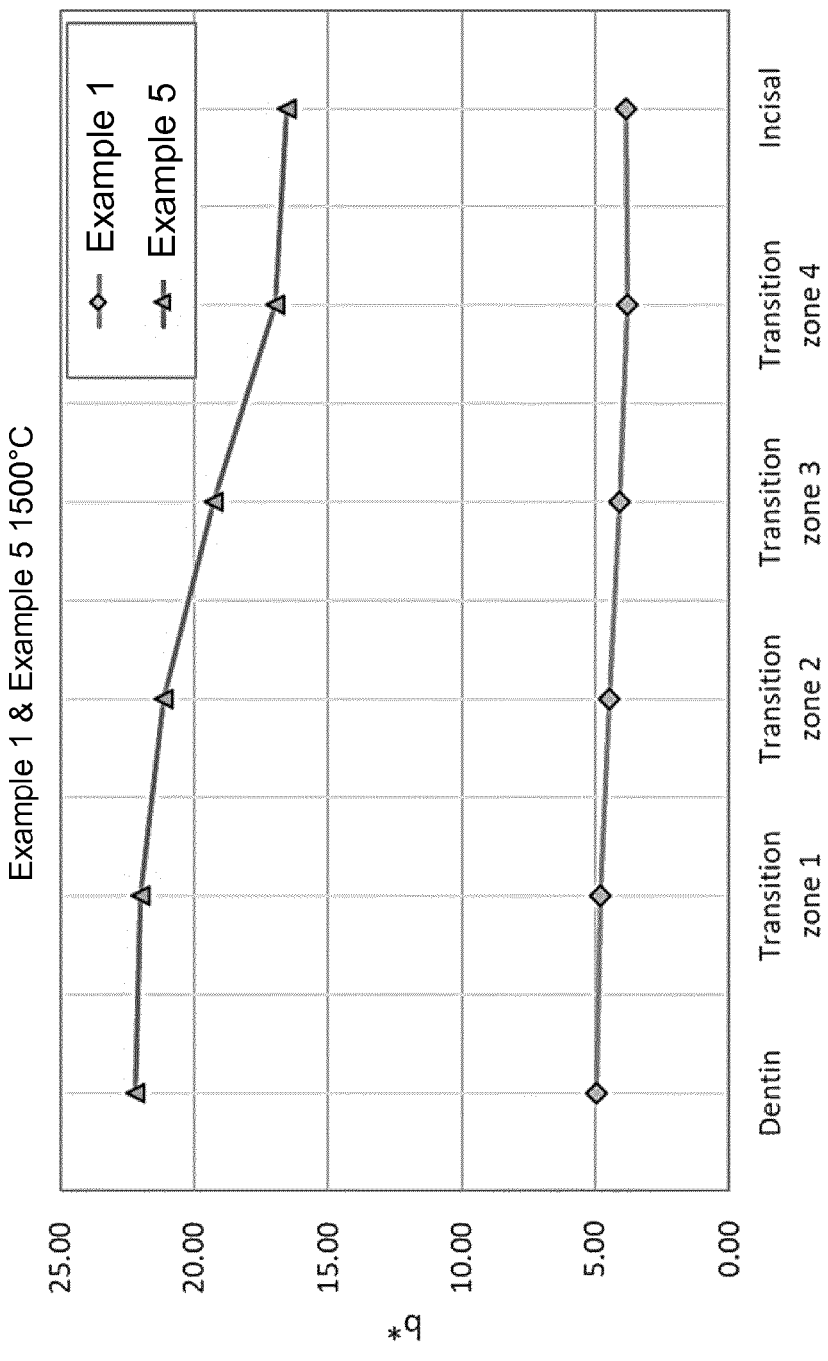

FIG. 38 shows gradient (b* values) of Example 1 and Example 5.

DETAILED DESCRIPTION OF THE DISCLOSURE

Although claimed subject matter is described herein in terms of certain embodiments and examples, other embodiments and examples, including embodiments and examples that do not provide all of the benefits and features set forth herein, are also within the scope of this disclosure. Various structural, logical, and process step may be made without departing from the scope of the disclosure.

Every numerical range given throughout this specification includes its upper and lower values, as well as every narrower numerical range that falls within it, as if such narrower numerical ranges were all expressly written herein, and, unless described otherwise, every value is included to the tenth of the value of the lower limit.

The present disclosure provides pre-sintered zirconia dental ceramic materials, sintered zirconia dental ceramic materials, and dental articles. The present disclosure also provides methods of making the pre-sintered dental zirconia dental ceramic materials and the sintered ceramic materials.

The present disclosure provides, in various examples, sintered zirconia dental materials and dental articles that that exhibit a smooth gradient transition of translucency and color between dentin to incisal regions or zones of the materials/articles to replicate natural dentition, utilizing a transition or gradient zone between the incisal and dentin zones, with no observable layers or demarcation within the gradient zone, or between the gradient and the incisal and dentin regions or zones, while still maintaining the desirable biaxial flexural strength typically associated with high-strength zirconia.

Smooth as used herein may mean that the function describing yttria composition and/or color and/or translucency (e.g., a gradient in yttria composition and/or color and/or translucency) in at least a portion (e.g., the portion between an incisal zone or dentin zone and the immediately adjacent transition zone) or all of the pre-sintered zirconia dental material, sintered zirconia dental material, or a dental article, in a direction normal to the longest dimension of the material, has a continuous first derivative or a continuous first derivative and second derivative.

In an aspect, the present disclosure provides pre-sintered zirconia dental ceramic materials and sintered zirconia dental ceramic materials. The pre-sintered zirconia dental ceramic materials comprise yttria and the pre-sintered zirconia dental ceramic materials have a yttria content gradient. A pre-sintered zirconia dental ceramic material can be sintered to form at least partially or fully sintered material, which may be a dental article.

Without intending to be bound by any particular theory, it is considered that the sintered zirconia dental ceramic materials of the present disclosure exhibit color or translucency gradient or color and translucency gradient resulting in esthetics similar to or of a natural tooth, without the use of a layered material.

A pre-sintered zirconia dental ceramic material has a gradient in yttria content in at least a portion or all of the pre-sintered zirconia dental ceramic material. A gradient in yttria content may be referred to as a gradient in yttria concentration. The gradient may be a continuous and uninterrupted gradient. The gradient may be smooth and/or have not discontinuities. The gradient may be in a direction normal to a longest dimension of the pre-sintered zirconia dental ceramic material.

A pre-sintered zirconia dental ceramic material may have different regions (which are also referred to herein as zones) with different gradient yttria content. An individual zone may have the same gradient as one or more of the other zones or each zone may have a different gradient. For example, the pre-sintered zirconia dental ceramic material comprises at least two or at least three zones where adjacent zones have different yttria content gradients.

Pre-sintered zirconia dental ceramic materials can comprise various amounts of yttria. In various examples, a pre-sintered zirconia dental ceramic material (or each independent zone of a pre-sintered zirconia dental material) has a yttria content (e.g., a yttria concentration) of 2 to 8 mol %, including all 0.1 mol % values and ranges therebetween. For example, the yttria content varies from 2 to 8 mol % in a gradient zone, which may be a transition zone. In various examples, a pre-sintered zirconia dental ceramic material has a yttria content (e.g., a yttria concentration) of 3 to 5 mol %. For example, the yttria content varies from is 3 to 5 mol % in a gradient zone, which may be a transition zone. Yttria mol % as used in reference to pre-sintered zirconia dental ceramic materials is the moles of Y divided by the sum of the moles of Y and Zr, where the result is multiplied by 100, or the moles of $Y_2O_3$ divided by the sum of the moles of moles of $Y_2O_3$ and $ZrO_2$, where the result is multiplied by 100.

In an example, the pre-sintered zirconia dental ceramic has no region in which there is a gradient yttria content having a dimension (e.g., a length) of 1 to 300 microns or less than or equal to 10%, 5%, or 1% of the ceramic (e.g., of the transition zone)) in a direction normal to the largest dimension of the ceramic that has a constant yttria content. In another example, the pre-sintered zirconia dental ceramic has no region having a dimension (e.g., a length) of 1 to 300 microns or less than or equal to 10%, 5%, or 1% of the ceramic (e.g., of the transition zone)) in a direction normal to the largest dimension of the ceramic that has a constant yttria content.

A pre-sintered zirconia dental ceramic material can have various gradients. Without intending to be bound by any particular theory, it is considered that the gradient in yttria content results in a pre-sintered zirconia dental ceramic material or a sintered zirconia dental ceramic material having one or more desirable features (e.g., one or more desirable optical features, one or more mechanical properties, or a combination thereof) described herein. A pre-sintered zirconia dental ceramic material may have a linear or non-linear gradient in yttria content in at least a portion or all of the pre-sintered zirconia dental ceramic material.

A pre-sintered zirconia dental ceramic material may have a gradient yttria content where the yttria concentration increases along the gradient from the first outer surface to the second outer surface. In an example, the pre-sintered zirconia dental ceramic has a first outer surface and a second outer surface opposite the first outer surface, and further comprising a yttria content between the first outer surface and the second outer surface, where the yttria content having a concentration of yttria that varies according to a gradient along a dimension from the first outer surface to the second outer surface, where the gradient is a linear gradient or a non-linear gradient.

A pre-sintered zirconia dental ceramic material may have non-linear yttria gradient that is described or approximated by (e.g., defined by) a function (i.e., an equation) or a combination of functions. In non-limiting examples, the gradient is described or approximated by (e.g., defined by) by the sum of two gradient functions (i.e., equations) chosen from linear gradients, non-linear gradients, and combinations thereof. Non-limiting examples of functions defining the non-linear gradient in yttria content in at least a portion or all of a pre-sintered zirconia dental ceramic material include exponential functions, which may define an exponential gradient, first-order polynomial functions, which may define first order polynomial gradients, second-order polynomial functions, which may define second-order polynomial gradients, third-order polynomial functions, which may define third-order polynomial gradients, power law polynomial functions, which may define power law polynomial gradients, logarithmic (e.g., logarithm) functions, which may define logarithmic (e.g., logarithm) gradients, or the like, or a combination thereof.

A pre-sintered zirconia dental ceramic material may have a linear or non-linear yttria gradient or comprise at least one region (e.g., a transition zone) that is described or approximated by one of the following functions (i.e., equations): $y=ax+b$ (a linear gradient), where $a=0.05-3$, including all 0.001 values and ranges therebetween, and $b=--50-10$, including all 0.1 values and ranges therebetween, (e.g., $y=0.51x-1.57$) or $y=-0.0167x^3+0.5286x^2-5.0119x+17.44$ (a non-linear gradient), where y is the yttria content. In the case the non-linear gradient function, this function is for a pre-sintered zirconia dental ceramic formed using 3Y-TZP and 5Y-ZP zirconia powders and the pre-sintered zirconia dental ceramic is in the form of a disc with a dimension of 16 mm normal to a longest dimension of the disc. While this specific example of a non-linear gradient is provided, it is within the purview of one skilled in the art to determine other mixtures of zirconia ceramic materials that can be described as a non-linear gradient.

The pre-sintered zirconia dental ceramic materials can have various form factors (e.g., shapes and/or sizes). In non-limiting examples, a pre-sintered zirconia dental ceramic is in the form of a disk, a block, blank, preformed dental restoration, preformed dental appliance, or the like. The pre-sintered zirconia dental ceramic materials can have various shapes and sizes. For example, a pre-sintered zirconia dental ceramic has at least one dimension (e.g., a thickness) of 10 to 30 mm (e.g., 14, 16, 18, 20, or 25 mm). For example, a pre-sintered zirconia dental ceramic material has a longest dimension (e.g. length, diameter, etc.) of 10 to 120 mm or 40 to 120 mm (e.g., a disc with diameter of 98.5 mm (+/−5%, 10%, or 20%).

A pre-sintered zirconia dental ceramic material may comprise a plurality of zones. Without intending to be bound by any particular theory, it is considered that some or all of the zones may correspond to various portions of a natural tooth. In various examples, a pre-sintered zirconia dental ceramic material comprises two or more zones or three or more zones. In various examples, only one of the zones has a gradient yttria content. In various examples, all of the zones has a gradient yttria content. In various examples, two or more or three or more of the zones have different yttria content, which independently may have a gradient yttria content. A zone may have a constant yttria content. In various examples, where the yttria concentration is described as constant (e.g., dentin zone, incisal zone, etc.), the change in yttria concentration along a portion or all of a direction normal to the longest dimension of the material is less than or equal to 2%, 1%, 0.5%, 0.1%, 0.05%, or 0.01%. In various examples, the function(s) describing the yttria composition in at least a portion (e.g., the portion between an incisal zone and/or dentin zone and the immediately adjacent transition zone) or all of the pre-sintered zirconia dental material, in a direction normal to the longest dimension of the material or article, is/are not discontinuous.

A pre-sintered zirconia dental ceramic material may comprise an incisal zone, a transition zone, and a dentin zone. A transition zone may have a linear or non-linear gradient of yttria content. In various examples, the difference in yttria concentration between the incisal zone and/or dentin zone and the immediately adjacent transition zone location, in a direction normal to the longest dimension of the material or article, is less than 10%, 5%, 1%, %, 0.5%, 0.1%, 0.05%, or 0.01%. An incisal zone and/or a dentin zone may have constant yttria content.

A transition zone may be disposed between an incisal zone and a dentin zone. An incisal zone may be adjacent to a transition zone, and the transition zone is adjacent to the dentin zone.

In various examples, a pre-sintered zirconia dental ceramic material has a first outer surface and a second outer surface opposite to the first outer surface and a dimension from the first outer surface to the second outer surface encounters, in order, an incisal zone, a transition zone, and a dentin zone. In various examples, the incisal zone has at least one dimension (e.g., a thickness) of 3 mm (+/−10% or 20%) and/or the transition zone has at least one dimension (e.g., a thickness) of 4 mm (+/−10% or 20%) and/or the dentin zone has at least one dimension (e.g., a thickness) of 7 (+/−10% or 20%) to 19 mm (+/−10% or 20%). The at least one dimension may be in a direction perpendicular to the longest dimension of the pre-sintered ceramic material. In various examples, the incisal zone has at least one dimension (e.g., a thickness) of 3 mm (+/−2 mm) and/or the transition zone has at least one dimension (e.g., a thickness) of 4 mm (+/−2 mm) and/or the dentin zone has at least one dimension (e.g., a thickness) of 3 (+/−2 mm) to 23 mm (+/−2 mm). The at least one dimension may be in a direction perpendicular to the longest dimension of the pre-sintered ceramic material.

A pre-sintered zirconia dental ceramic may have various microstructure features. A pre-sintered zirconia dental ceramic material may be porous. For example, a pre-sintered zirconia dental ceramic material has a density of 40 to 70% (e.g., 50 to 60%, 54 to 57%, or 55 to 56%) of the sintered zirconium dioxide theoretical density (e.g., 6.1 $g/m^2$, for 3Y-TZP). For example, a pre-sintered zirconia dental ceramic material has porosity of 30 to 60% (e.g., 40 to 50%, 43 to 47%, or 44 to 45%). Density and porosity can be determined by methods known in the art.

A pre-sintered zirconia dental ceramic material or a sintered zirconia dental ceramic material (e.g., an incisal zone, a dentin zone, a transition zone, or a combination thereof of a pre-sintered zirconia dental ceramic material or a sintered zirconia dental ceramic material) can have various compositions. A pre-sintered zirconia dental ceramic material or a sintered zirconia dental ceramic material (e.g., an incisal zone, a dentin zone, a transition zone, or a combination thereof of a pre-sintered zirconia dental ceramic material or a sintered zirconia dental ceramic material) may comprise, in addition to yttria (e.g., $Y_2O_3$) and zirconia (e.g., $ZrO_2$), one or more additives, which may be coloring additives (examples of which are described herein), one or more sintering enhancer (e.g., alumina (e.g., $Y_2O_3$), magnesium oxide (e.g., MgO), or the like, or a combination thereof), and one or more sintering inhibitor (e.g., lanthanum oxide (e.g., $La_2O_3$), or the like, or a combination thereof).

In various examples, a pre-sintered zirconia dental ceramic material or a sintered zirconia dental ceramic material has the following composition:

| | |
|---|---|
| zirconia (e.g., $ZrO_2$) | 80-85% by weight |
| yttria (e.g., $Y_2O_3$) | less than 4.5% to lest than or equal to 7% by weight |
| optionally, hafnium oxide (e.g., $HfO_2$) | less than or equal to 5% by weight |
| optionally, alumina (e.g., $Al_2O_3$) | less than or equal to 1% by weight |
| optionally, other oxides | less than 1.5% by weight, where the % by weight | values are based on the total weight of the material. In certain of these examples, the amount of zirconia may be the remainder (making the sum of all of the components equal 100%) based on the amounts of the non-zirconia components and/or one or more or all of the optional components are present. In various other examples, an incisal zone of a pre-sintered zirconia dental ceramic material or a sintered zirconia dental ceramic material has the following composition:

| | |
|---|---|
| zirconia (e.g., $ZrO_2$) | greater than 90% by weight |
| yttria (e.g., $Y_2O_3$) | 9.15 to 9.55% by weight |
| optionally, silica (e.g., $SiO_2$) | 0.04 to 0.06% by weight |
| optionally, iron oxide (e.g., $Fe_2O_3$) | less than or equal to 0.02% by weight |
| optionally, manganese oxide (e.g., $Mn_2O_3$) | less than or equal to 0.0005% by weight |
| optionally, chromium oxide (e.g., $Cr_2O_3$) | less than or equal to 0.002% by weight |
| optionally, praseodymium oxide (e.g., $Pr_2O_3$) | less than or equal to 0.002% by weight |
| optionally, terbium oxide (e.g., $Tb_2O_3$) | less than or equal to 0.005% by weight |
| optionally, erbium oxide (e.g., $Er_2O_3$) | less than or equal to 0.5% by weight |
| optionally, magnesium (e.g., MgO) | 0.02 to 0.03% by weight |
| optionally, alumina (e.g., $Al_2O_3$) | 0.01 to 0.02% by weight, | and/or
an dentin zone of a pre-sintered zirconia dental ceramic material or a sintered zirconia dental ceramic material has the following composition:

| | |
|---|---|
| zirconia (e.g., $ZrO_2$) | 87 to 95% by weight |
| yttria (e.g., $Y_2O_3$) | 5 to 5.5% by weight |
| alumina (e.g., $Al_2O_3$) | 0.04 to 0.06% by weight |
| optionally, silica (e.g., $SiO_2$) | less than or equal to 0.02% by weight |
| optionally, iron oxide (e.g., $Fe_2O_3$) | less than or equal to 0.02% by weight |
| optionally, manganese oxide (e.g., $Mn_2O_3$) | less than or equal to 0.002% by weight |
| optionally, chromium oxide (e.g., $Cr_2O_3$) | less than or equal to 0.0045% by weight |
| optionally, praseodymium oxide (e.g., $Pr_2O_3$) | less than or equal to 0.005% by weight |
| optionally, terbium oxide (e.g., $Tb_2O_3$) | less than or equal to 0.02% by weight |
| optionally, erbium oxide (e.g., $Er_2O_3$) | less than or equal to 0.7%, |
| optionally, lanthanium oxide (e.g., $La_2O_3$) | 0.45 to 0.65% by weight, | or
a dentin zone has the following composition:

| | |
|---|---|
| zirconia (e.g., $ZrO_2$) | 87 to 95% by weight |
| yttria (e.g., $Y_2O_3$) | 5 to 5.5% by weight |
| alumina (e.g., $Al_2O_3$) | 0.04 to 0.06% by weight |
| optionally, silica (e.g., $SiO_2$) | less than or equal to 0.02% by weight |
| optionally, iron oxide (e.g., $Fe_2O_3$) | less than or equal to 0.1% by weight |
| optionally, manganese oxide (e.g., $Mn_2O_3$) | less than or equal to 0.002% by weight |
| optionally, chromium oxide (e.g., $Cr_2O_3$) | less than or equal to 0.005% by weight |
| optionally, praseodymium oxide (e.g., $Pr_2O_3$) | less than or equal to 0.005% by weight |
| optionally, terbium oxide (e.g., $Tb_2O_3$) | less than or equal to 0.002% by weight |
| optionally, erbium oxide (e.g., $Er_2O_3$) | less than or equal to 0.7%, |
| optionally, lanthanium oxide (e.g., $La_2O_3$) | 0.45 to 0.65% by weight, | where the % by weight values are based on the total weight of the material and one or more of the components may be present at a different weight percentage in one of the regions relative to the other region. In various other examples, an incisal zone of a pre-sintered zirconia dental ceramic material or a sintered zirconia dental ceramic material has the following composition:

| zirconia (e.g., $ZrO_2$) | greater than 89% by weight |
|---|---|
| yttria (e.g., $Y_2O_3$) | 9.15 to 9.55% by weight |
| optionally, silica (e.g., $SiO_2$) | 0.04 to 0.06% by weight |
| optionally, iron oxide (e.g., $Fe_2O_3$) | less than or equal to 0.07% by weight |
| optionally, manganese oxide (e.g., $Mn_2O_3$) | less than or equal to 0.0005% by weigh |
| optionally, chromium oxide (e.g., $Cr_2O_3$) | less than or equal to 0.002% by weight |
| optionally, praseodymium oxide (e.g., $Pr_2O_3$) | less than or equal to 0.002% by weight |
| optionally, terbium oxide (e.g., $Tb_2O_3$) | less than or equal to 0.005% by weight |
| optionally, erbium oxide (e.g., $Er_2O_3$) | less than or equal to 0.5% by weight |
| optionally, magnesium (e.g., MgO) | 0.005 to 0.03% by weight |
| optionally, alumina (e.g., $Al_2O_3$) | 0.01 to 0.05% by weight | where the % by weight values are based on the total weight of the material and one or more of the components may be present at a different weight percentage in one of the regions relative to the other region. In these examples, the amount of zirconia may be the remainder (making the sum of all of the components 100%) based on the amounts of the non-zirconia components and/or one or more or all of the optional components are present.

A pre-sintered zirconia dental ceramic material or a sintered zirconia dental ceramic material (e.g., an incisal zone, a dentin zone, a transition zone, or a combination thereof of a pre-sintered zirconia dental ceramic material or a sintered zirconia dental ceramic material) may comprise, in addition to yttria (e.g., $Y_2O_3$) and zirconia (e.g., $ZrO_2$), one or more additives, which may be coloring additives, one or more sintering enhancer, and one or more sintering inhibitor.

A pre-sintered zirconia dental ceramic material may be made by using a combination of yttria-containing zirconia materials having different yttria concentration. In various examples, a pre-sintered zirconia dental ceramic material is formed from a mixture of two or more or three or more yttria-containing zirconia materials. In various examples, a pre-sintered zirconia dental ceramic material is formed by a method of the present disclosure.

In an aspect, the present disclosure provides methods of making pre-sintered zirconia dental ceramic materials. Pre-sintered zirconia dental ceramic materials of the present disclosure can be made by a method of the present disclosure. In various examples, a pre-sintered zirconia dental ceramic material is made by a method of the present disclosure.

In various examples, a method of making a pre-sintered zirconia dental ceramic material having a gradient yttria content in at least a portion or all of the pre-sintered zirconia dental ceramic material comprises: forming a monolithic structure (e.g., a green structure or a mold) from at least a first zirconia ceramic powder having a first yttria content and a second zirconia ceramic powder having a second yttria content, wherein the first yttria content is different than the second yttria content; subjecting the monolithic structure to uniaxial pressing at a pressure of 75-125 MPa, including all 0.1 MPa values and ranges therebetween, (e.g., to form a green compact structure); subjecting the uniaxially pressed monolithic structure to cold isotactic pressing at a pressure of 200400 MPa including all 0.1 MPa values and ranges therebetween, (e.g., at ambient temperature, such as, for example, 18-25° C.); and heating (e.g., debinding and pres-intering) the uniaxial pressed and cold isostatic pressed monolithic structure to a temperature of 900-1100° C. including all 0.1° C. values and ranges therebetween, (e.g., 950-1050° C.), where a pre-sintered zirconia dental ceramic material is formed. The heating may be carried out for a holding time of 1 to 4 hours, including all integer minute values and ranges therebetween, which may be at the maximum heating temperature.

Various zirconia ceramic powders may be used. Mixtures of zirconia ceramic powders may be used. The zirconia ceramic powders may be tetragonal, cubic or monoclinic zirconia ceramic powders or a mixture thereof zirconia ceramic powders. A zirconia ceramic powder may be yttria-doped zirconia ceramic powder (which may be referred to as Y-TZP (tetragonal zirconia polycrystal) or Y-ZP (zirconia polycrystal)). For example, a yttria-doped tetragonal or tetragonal-cubic or tetragonal-monoclinic or tetragonal-cubic-monoclinic zirconia ceramic powder comprises $Y_2O_3$-doped zirconia polycrystals. The zirconia ceramic powders may further comprise (e.g., in addition to $Y_2O_3$) various stabilizing dopants/agents. Non-limiting examples of stabilizing dopants/agents include Ce, Ca, Mg, Yb, Er, and oxides thereof, and combinations thereof. A zirconia ceramic powder may comprise small amounts of alumina, such as, for example, 0.25 wt. %, as a sintering aid. The zirconia ceramic powders may be granular. Suitable zirconia ceramic powders are commercially available or can be made by methods known in the art.

The zirconia ceramic powders may have a desirable particle size distribution. In various examples, one or more or all of the zirconia ceramic powder(s) has/have less than 1% by weight of particles having a size (e.g., longest dimension) of greater than 400 microns or greater than 200 microns. In an example, one or more or all of the zirconia ceramic powder(s) does not have particles having a size (e.g., longest dimension) of greater than 200 microns.

The zirconia ceramic powders can have various yttria content. In various examples, the zirconia ceramic powders are independently chosen from 0Y to 10Y, including all 0.1 Y values and ranges therebetween, (e.g., 1.5Y to 10Y) (where Y is mol % of yttria in the powders), including all 0.01 Y values and ranges therebetween. In various examples, the zirconia ceramic powders are independently chosen from 1.5Y, 2Y, 2.8Y, 3Y, 4.25Y, 4.5Y, 5Y, 5.5Y, etc, zirconia ceramic powders. In an example, the zirconia ceramic powders are 3 Y-TZP and 5 Y-ZP zirconia ceramic powders.

A zirconia powder may comprise a mixture of two or more zirconia powders having at least two different phases (e.g., a mixture of a zirconia powder having a tetragonal phase and a zirconia powder having a cubic phase, where the zirconia powders have the same nominal composition (e.g., the same yttria content) or different nominal composition (e.g., different yttria content). As an illustrative example, a 5Y-ZP powder is a mixture of 5Y-ZP powders having two different phases (e.g., tetragonal and cubic phases, for example, a 45:55 to 55:45 or about 50:50 mixture of tetragonal and cubic phases).

For example, one or more of the zirconia ceramic powder (s) comprises non-coloring dopants/agents as lanthanum ions (e.g., which may be provided by $La_2O_3$ or $La(NO_3)_3 \cdot 6H_2O$). In various examples, at least one zirconia ceramic powder comprises lanthanum ions (e.g., which may be provided by $La_2O_3$ or $La(NO_3)_3 \cdot 6H_2O$, etc.) and at least one different zirconia ceramic powder comprise non-coloring magnesium ions (e.g., which may be provided by MgO or $Mg(NO_3)_2 \cdot 6H_2O$) and/or aluminum ions (e.g., which may be provided by $A_2O_3$ or $Al(NO_3)_3 \cdot 9H_2O$).

One or more of the zirconia ceramic powders may be colored. Combinations of zirconia ceramic powders with different color (e.g., comprising one or more different coloring ions) may be used. A zirconia ceramic powder may comprise one or more coloring agents. The coloring agent(s) may be present as free or solute element(s), or as a compound(s) of the element(s).

Non-limiting examples of coloring agent(s) include the lanthanide series of elements and compounds thereof, excluding synthetic and radioactive elements, groups 5 to 11 of the periodic table and compounds thereof, excluding synthetic and radioactive elements, and Ti or Sc, and the like, and compounds thereof (e.g., oxides thereof). For the lanthanide series this includes: lanthanum; cerium; praseodymium; neodymium; samarium; europium; gadolinium; terbium; dysprosium; holmium; erbium; thulium; ytterbium; and lutetium. For groups 5 to 11 of the Periodic Table, this includes: vanadium; niobium; tantalum; chromium; molybdenum; tungsten; manganese; rhenium; bohrium; iron; ruthenium; osmium; cobalt; rhodium; iridium; nickel; palladium; platinum; copper; silver; and gold. The coloring agent(s) may be present as ions.

Aqueous solutions of various salts can be used as coloring substances. Water-soluble salts, which may be hydrate salts or anhydrous salts, of d- or f-elements of the periodic table described above can be utilized. Nitrate or chloride hydrates of these elements are non-limiting examples of coloring salts. Non-limiting examples of coloring salts that can be used are $Pr(NO_3)_3 \cdot HO$, $Fe(NO_3)_3 \cdot 9H_2O$, $FeCl_3 \cdot 6H_2O$ $Tb(NO_3)_3 \cdot 5H_2O$, $Er(NO_3)_3 \cdot 5H_2O$, $ErCl_3 \cdot 6H_2O$, $Mn(NO_3)_2 \cdot 4H_2O$, $MnCl_2 \cdot 4H_2O$, $Cr(NO_3)_3 \cdot 9H_2O$, $CrCl_3 \cdot 6H_2O$, and anhydrous analogs thereof, and the like.

Colored zirconia ceramic powders are commercially available or can be made by methods known in the art. In an example, one or more or all of the zirconia ceramic powders is/are in granulate form and the granules are brought into contact with a solution that contains metal ions and/or metal complexes.

A monolithic structure comprises pressed or compacted zirconia ceramic powders. A monolithic structure may be referred to as a green body or a mold. The monolithic structure may be formed by adding, in addition to the zirconia ceramic powders, one or more additional components. Non-limiting examples of additional components include coloring agents, stabilizing dopants/agents, which may be, one or more sintering enhancer (e.g., alumina (e.g., $Al_2O_3$), magnesium oxide (e.g., MgO), or the like, or a combination thereof), one or more sintering inhibitor (e.g., lanthanum oxide (e.g., $La_2O_3$), or the like, or a combination thereof), or the like, or a combination thereof.

The monolithic structure or resulting pre-sintered zirconia dental material may comprise a plurality of zones. In various examples, a monolithic structure comprises two or more zones or three or more zones. In various examples, only one of the zones has a gradient yttria content and the other zones do not have a gradient yttria content. In various examples, all of the zones has a gradient yttria content. In various examples, two or more or three or more of the zones have different yttria content, which independently may have a gradient yttria content.

A monolithic structure or resulting pre-sintered zirconia dental material may comprise an incisal zone, a transition zone, and a dentin zone. A transition zone may have a linear or non-linear gradient in yttria content. Without intending to be bound by any particular theory, it is considered that some or all of the zones may correspond to various portions of a natural tooth.

A transition zone may be disposed between an incisal zone and a dentin zone. An incisal zone may be adjacent to a transition zone, and the transition zone is adjacent to the dentin zone.

A monolithic structure may be formed by mixing two different ceramic powders having a first yttria content and a second yttria content, where the first yttria content is greater than the second yttria content (e.g., 5Y and 3Y or 5Y-ZP and 3Y-TZP zirconia ceramic powders). A monolithic structure may be formed by mixing two different ceramic powders having a first yttria content and a second yttria content (e.g., 5Y and 3Y or 5Y-ZP and 3Y-TZP zirconia ceramic powders) in a selected ratio to form a transition zone and/or using the ceramic powder having a first yttria content (e.g., 3Y or 3Y-TZP zirconia ceramic powder, which may comprise alumina and/or magnesium oxide) to form a dentin zone and/or using the ceramic powder having a first yttria content (e.g., 5Y or 5Y-ZP zirconia ceramic powder, which may comprise lanthanum oxide) to form an incisal zone.

In various examples, a monolithic structure or resulting pre-sintered zirconia dental material has a first outer surface and a second outer surface opposite to the first outer surface and a dimension from the first outer surface to the second outer surface encounters, in order, an incisal zone, a transition zone, and a dentin zone. In various examples, the incisal zone has at least one dimension (e.g., a thickness) of 3 mm (+/−10% or 20%) and/or the transition zone has at least one dimension (e.g., a thickness) of 4 mm (+−10% or 20%) and/or the dentin zone has at least one dimension (e.g., a thickness) of 7 (+/−10% or 20%) to 19 mm (+/−10% or 20%). The at least one dimension may be in a direction perpendicular to the longest dimension of the monolithic structure. In various examples, the incisal zone has at least one dimension (e.g., a thickness) of 3 mm (+/−2 mm) and/or the transition zone has at least one dimension (e.g., a thickness) of 4 mm (+/−2 mm) and/or the dentin zone has at least one dimension (e.g., a thickness) of 3 (+/−2 mm) to 23 mm (+/−2 mm).

The pre-sintered zirconia dental ceramic may be sintered to form a sintered (e.g., partially sintered or fully/dense sintered) zirconia dental ceramic. In various examples, a method further comprises sintering (e.g., fully/dense sintering) the pre-sintered zirconia dental ceramic, wherein a sintered zirconia dental ceramic is formed. Selection of suitable sintering conditions is within the purview of one skilled in the art.

A pre-sintered zirconia dental ceramic material, which may be in the form of a blank, may be shaped into a dental shaped part. In various examples, the pre-sintered zirconia dental ceramic material, which may be in the form of a blank, is millable using milling equipment available in a dental lab or dental practice, including a chairside milling system or larger dental lab milling system. For example, the shaping into a dental shaped part takes place in a dental laboratory or dental clinic. The shaping may take place by milling or grinding, for example, by means of a CAD/CAM unit. The, thus-obtained enlarged preform of a dental shaped part of the dental restoration is may be then sintered.

Sintering may be carried out at various temperatures. For example, sintering is carried out at a temperature of 1200° C. to 1600° C., including all 0.1° C. values and ranges therebetween. For example, the dense-sintering is carried out at 1300° C. to 1550° C. or 1400° C. to 1500° C. The duration of the sintering step may last, for example, for 5 minutes to 2 hours (e.g., 10 to 30 minutes). A complete standard sintering process with heating and, optionally, cooling generally lasts approximately 8-10 hours. A complete fast sintering process generally takes 2-5 hours. The milling process may be carried out such that the dental shaped part displays an excess that takes into account the shrinkage of the shaped part during the sintering. The sintering may be carried out using microwave energy or inductive heating, which typically leads to a further shortening of the process times. The prepared dental shaped part may represent the finished dental restoration, or it can be processed further, such as, for example, it is provided with a veneer in order to produce the finished dental restoration.

In an aspect, the present disclosure provides sintered zirconia dental ceramic materials. Sintered zirconia dental ceramic material of the present disclosure can be made by a method of the present disclosure. In various examples, a sintered zirconia dental ceramic material is made by a method of the present disclosure.

A sintered zirconia material can have the same composition (e.g., elemental composition) as described herein for pre-sintered materials. In various examples, a sintered zirconia material has the same composition (e.g., elemental composition) as described herein for pre-sintered materials.

A sintered zirconia dental ceramic material may be a partially sintered or fully sintered zirconia dental ceramic material. All references to a sintered zirconia dental ceramic material or materials herein, unless otherwise stated, include both partially-sintered or fully-sintered zirconia dental ceramic material(s). For example, a fully sintered 3Y-TZP is fully sintered if the density is greater that 6.0 g/cm$^3$ (e.g., as measured according to ISO 13356) or typically greater than 99% of the theoretical density (TD) of the material (e.g., as measured according to ISO 13356). The pre-sintered density below is a partially sintered state is greater than the pre-sintered density. Typically, the pre-sintered density is in the range of 2.9-3.4 g/cm$^3$.

A sintered zirconia dental ceramic material may be a material produced from a pre-sintered zirconia dental ceramic material in a heat treatment process (e.g., sintering), wherein the crystal portion is very largely retained and only a small portion, in most cases well below 5 vol-% glass phase portion, forms between the individual crystals.

A sintered zirconia dental ceramic may comprises a plurality of zones. The zones may correspond to the zones of the monolith and/or pre-sintered zirconia dental materials from which the sintered zirconia dental material is made. A zone may have different composition and/or one or more different properties (e.g., physical/mechanical property(ies), optical property(ies), or a combination thereof) that one or more of the other zones. In various examples, a sintered zirconia dental ceramic comprises two or more or three or more zones.

A sintered zirconia dental ceramic may comprise an incisal zone, a transition zone, and a dentin zone. The transition zone may be disposed between the incisal zone and the dentin zone and/or the incisal zone is adjacent to the transition zone, and the transition zone is adjacent to the dentin zone.

In various examples, the sintered zirconia dental ceramic has a first outer surface and a second outer surface opposite to the first outer surface and a dimension from the first outer surface to the second outer surface encounters, in order, an incisal zone, a transition zone, and a dentin zone. The incisal zone may have at least one dimension (e.g., a thickness) of 3 mm (+/−10% or 20%) and/or the transition zone may have at least one dimension (e.g., a thickness) of 4 mm (+/−10% or 20%) and/or the dentin zone may have at least one dimension (e.g., a thickness) of 7 (+/−10% or 20%) to 19 mm (+/−10% or 20%). In various examples, the incisal zone has at least one dimension (e.g., a thickness) of 3 mm (+/−2 mm) and/or the transition zone has at least one dimension (e.g., a thickness) of 4 mm (+/−2 mm) and/or the dentin zone has at least one dimension (e.g., a thickness) of 3 (+/−2 mm) to 23 mm (+/−2 mm). The at least one dimension may be in a direction perpendicular to the longest dimension of the pre-sintered ceramic material. The at least one dimension may be in a direction perpendicular to the longest dimension of the sintered zirconia dental ceramic material.

It may be desirable for a sintered zirconia dental ceramic to have a dentin zone that is darker than the incisal zone and an incisal zone that is more translucent than the dentin zone. As an illustrative example, such a sintered zirconia dental ceramic material can be formed by sintering a pre-sintered zirconia dental ceramic material formed by mixing 5Y or 3Y zirconia ceramic powders in a selected ratio to form a transition zone and/or using 3Y zirconia ceramic powder (which may comprise lanthanum oxide and, optionally, one or more coloring ions) to form a dentin zone and/or using 5Y zirconia ceramic powder (which may comprise alumina and/or magnesium oxide and, optionally, one or more coloring ions) to form an incisal zone.

A sintered zirconia dental ceramic material can have various gradients in yttria content. One or more or all of the gradients may correspond to the gradients of the monolith and/or pre-sintered zirconia dental materials from which the sintered zirconia dental material is made. A sintered zirconia dental ceramic material may have a linear or non-linear gradient in yttria content in at least a portion or all of the sintered zirconia dental ceramic material. In the case of a sintered zirconia dental ceramic material having a plurality of zones, the gradient yttria content may be different in at least two of the zones or at least three of the zones.

A sintered zirconia dental ceramic material may have a gradient yttria content where the yttria concentration increases along the gradient from the first outer surface to the second outer surface. In an example, the sintered zirconia dental ceramic has a first outer surface and a second outer surface opposite the first outer surface, and further comprising a yttria content between the first outer surface and the second outer surface, the yttria content having a concentration of yttria that varies according to a gradient along a dimension from the first outer surface to the second outer surface, wherein the gradient is a linear gradient or a non-linear gradient.

A sintered zirconia dental ceramic material may have non-linear yttria gradient that is described or approximated by (e.g., defined by) a function (i.e., an equation) or a combination of functions. In non-limiting examples, the gradient is described or approximated by (e.g., defined by) the sum of two exponential gradient functions (i.e., equations) chosen from linear gradients, non-linear gradients, and combinations thereof. Non-limiting examples of functions defining the non-linear gradient in yttria content in at least a portion or all of a sintered zirconia dental ceramic material include exponential functions, which may define an exponential gradient, first-order polynomial functions, which may define first order polynomial gradients, second-order polynomial functions, which may define second-order polynomial gradients, third-order polynomial functions, which may define third-order polynomial gradients, power law polynomial functions, which may define power law polynomial gradients, logarithmic (e.g., logarithm) functions, which may define logarithmic (e.g., logarithm) gradients, or the like, or a combination thereof.

Figure 1:
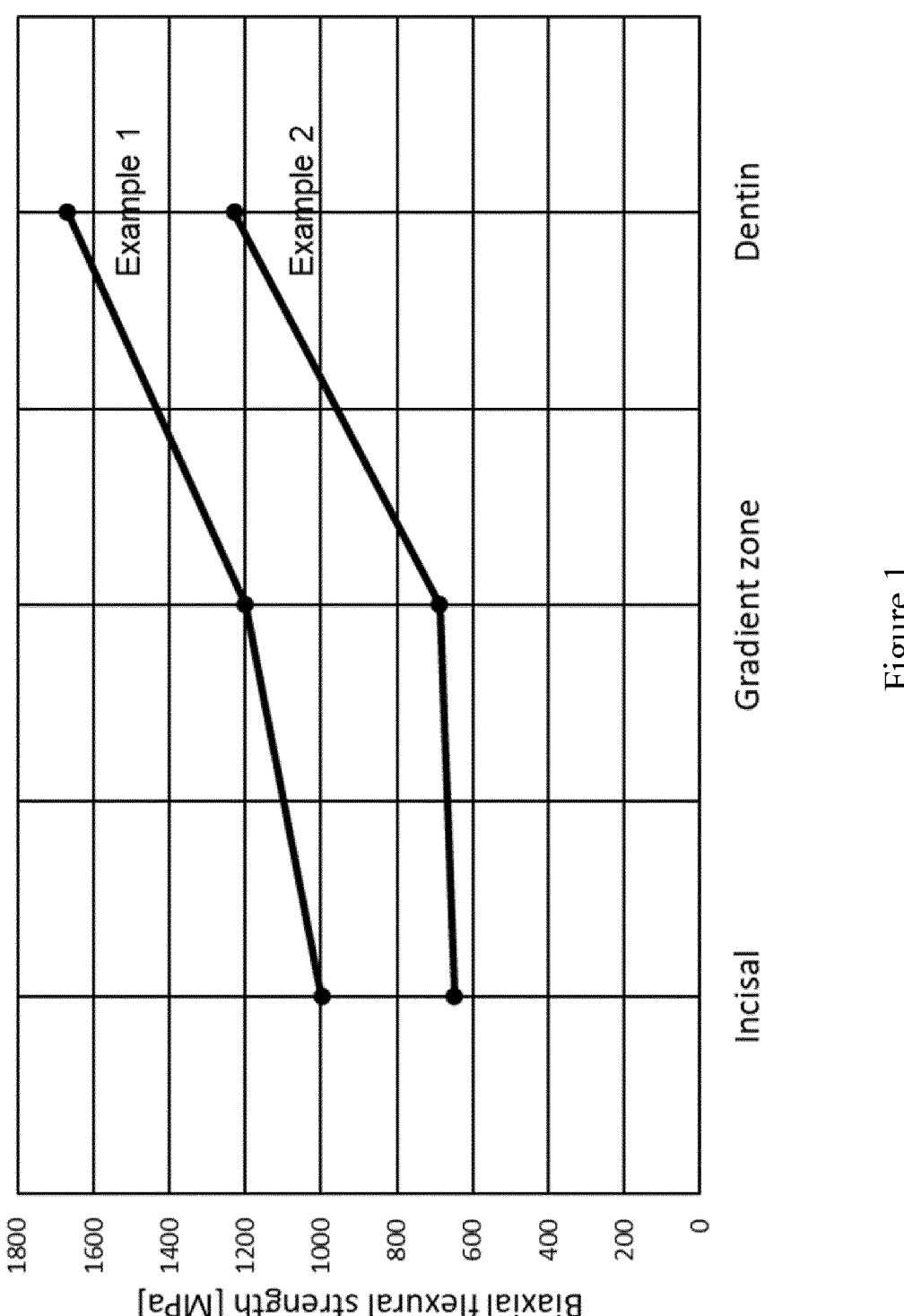
FIG. 1 shows flexural strength of examples of a Type II pre-sintered zirconia dental ceramic material (Example 1 and Example 2).
Figure 2:
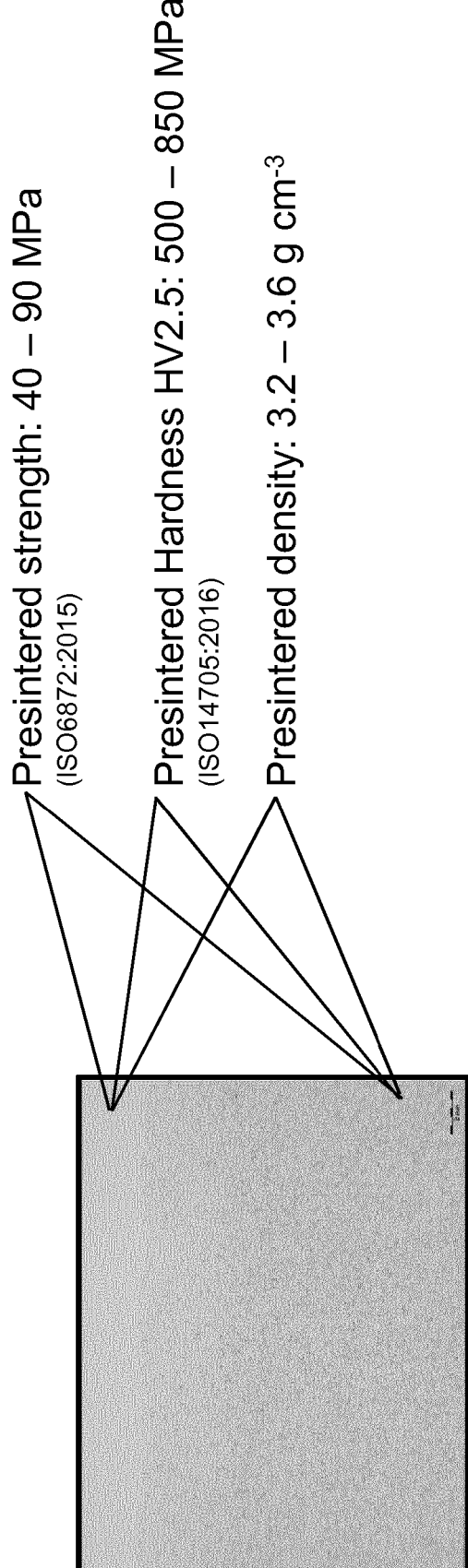
FIG. 2 shows a pre-sintered body stepless color and translucency gradient. The body is in the green state using indication color: not pre-sintered, yet in the pre-sintered state, the material is substantially white L*value>99%, in the dentin, as well as in the incisal part.
Figure 3:
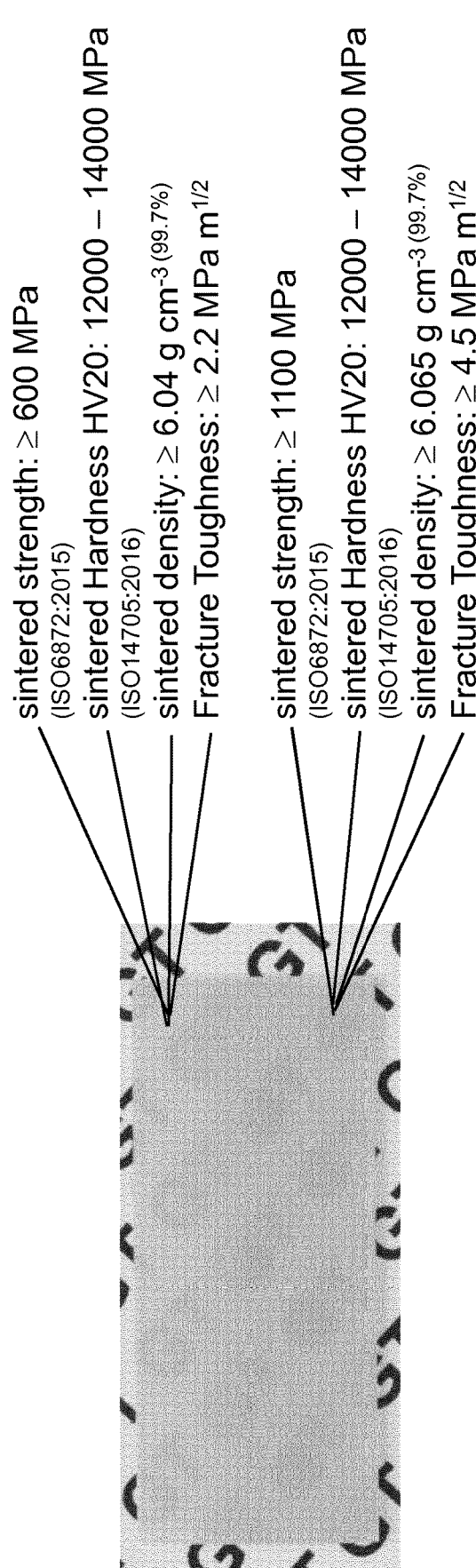
FIG. 3 shows a sintered body with a stepless color and translucency gradient. The opacity difference between dentin to incisal zone is at least 7% at 1 mm, even for the least color shade of Example 1.
Figure 4:
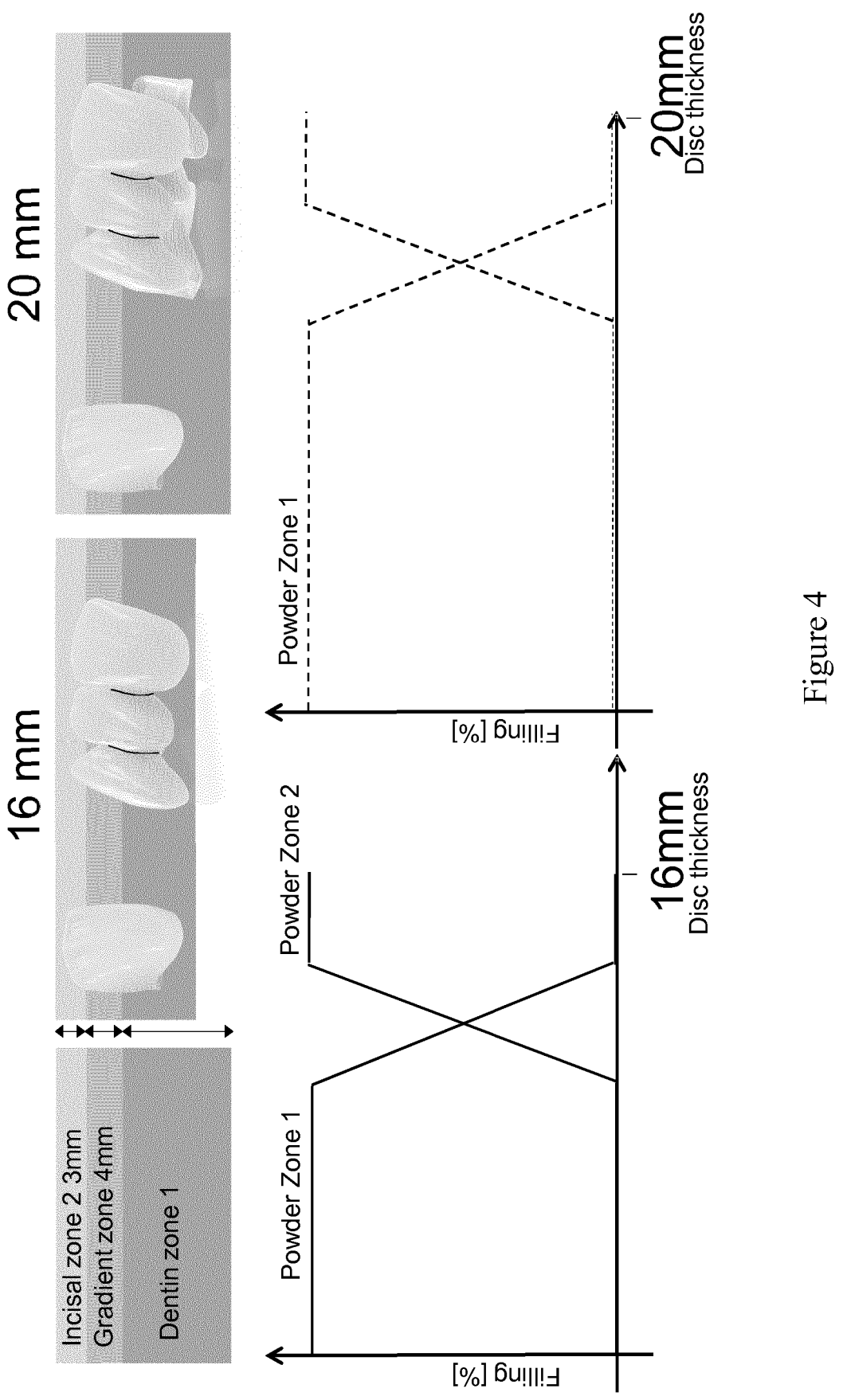
FIG. 4 shows an example of sintered zirconia dental ceramic formed into a shape of a dental restoration, with a corresponding charts and graph demonstrating the zone concept and the corresponding powder filling process.
Figure 5:
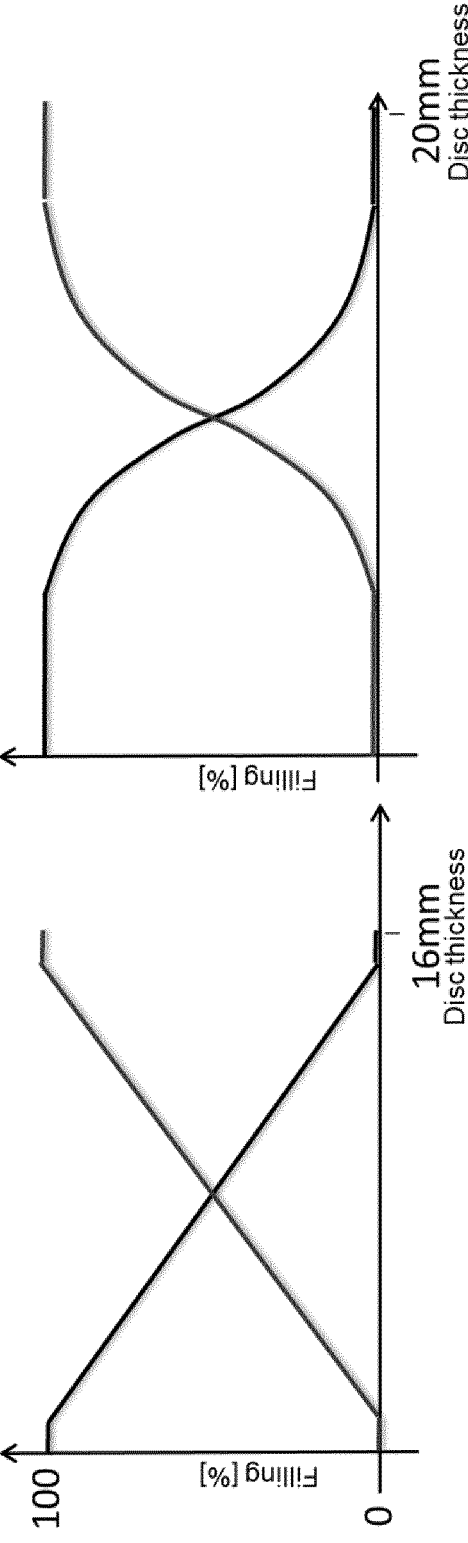
FIG. 5 shows principle diagrams of linear (e.g. 16 mm) and non-linear (e.g. 20 mm) powder filling process.
Figure 6:
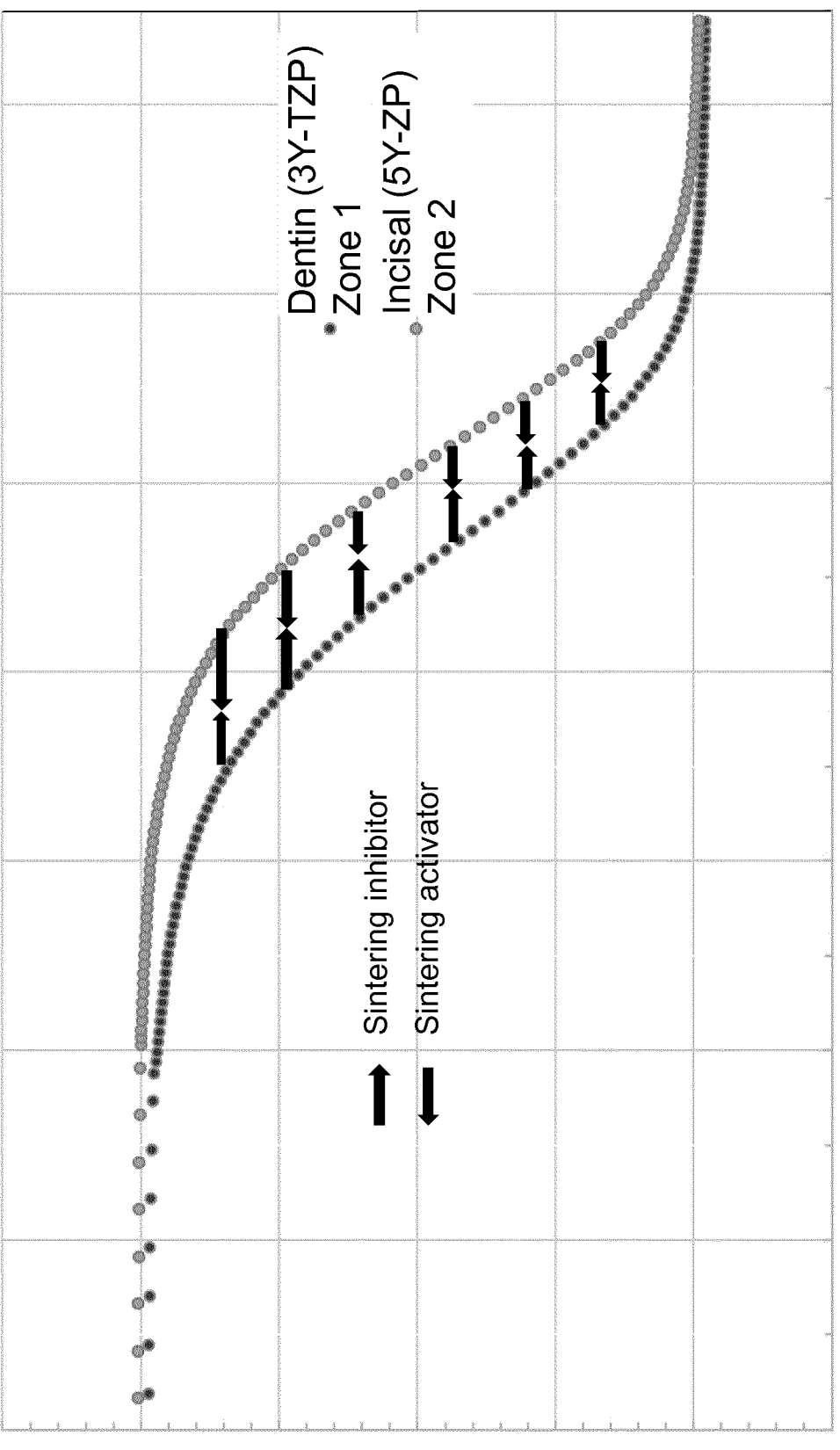
FIG. 6 shows adjustments of the sintering kinetics.
Figure 12:
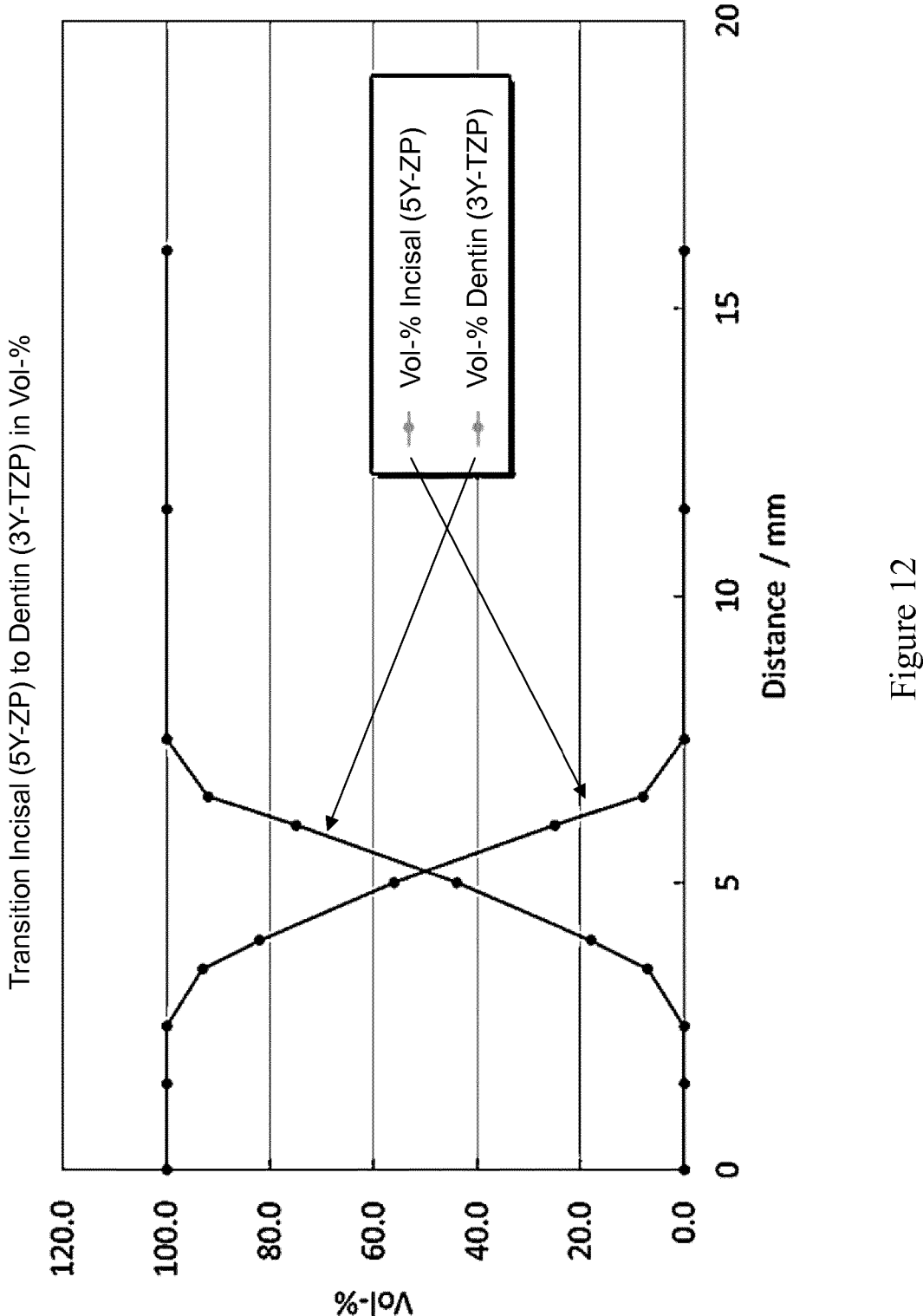
FIG. 12 shows interpolation of powder distribution.
Figure 13:
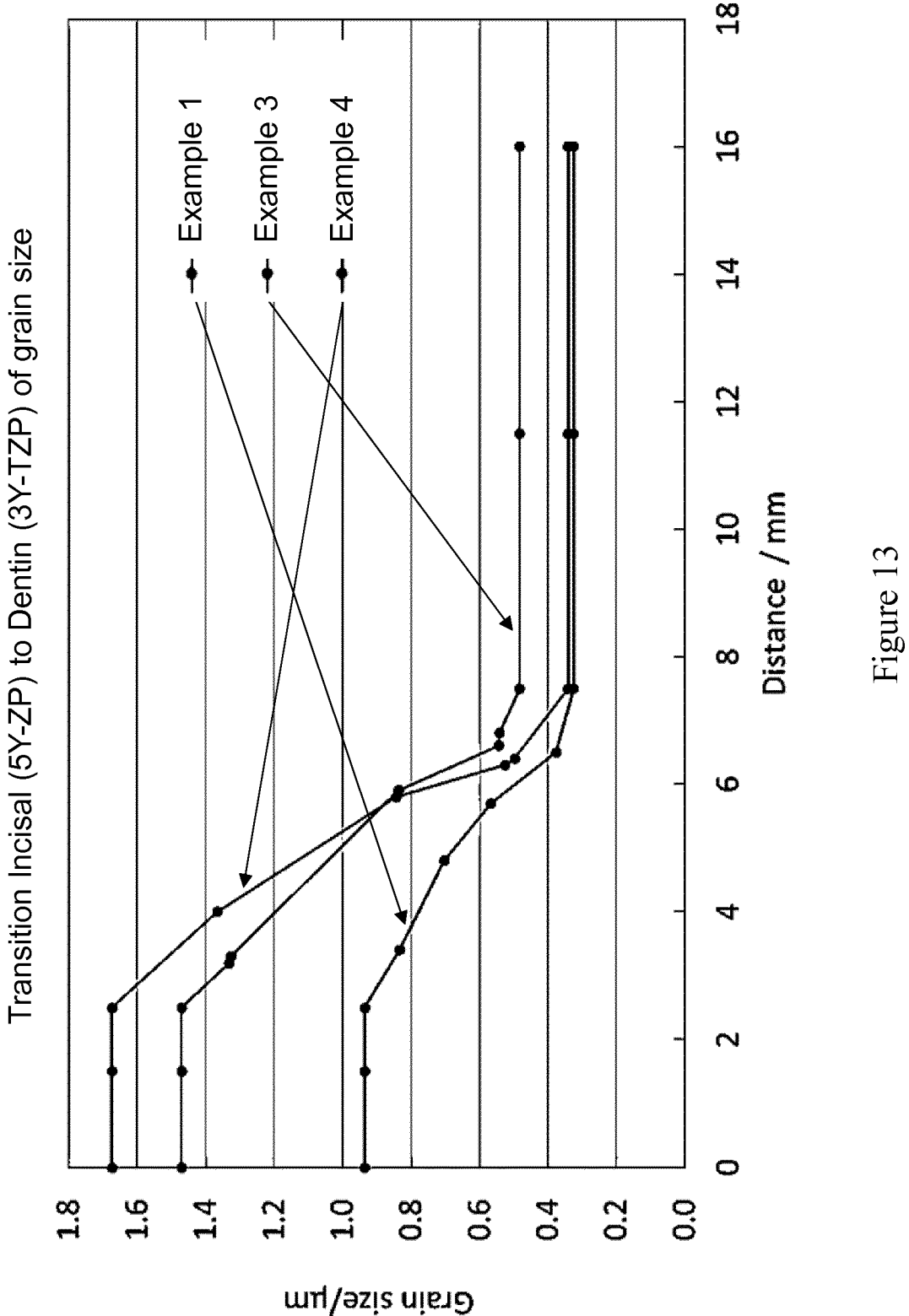
FIG. 13 shows interpolation of grain size distribution.
Figure 14:
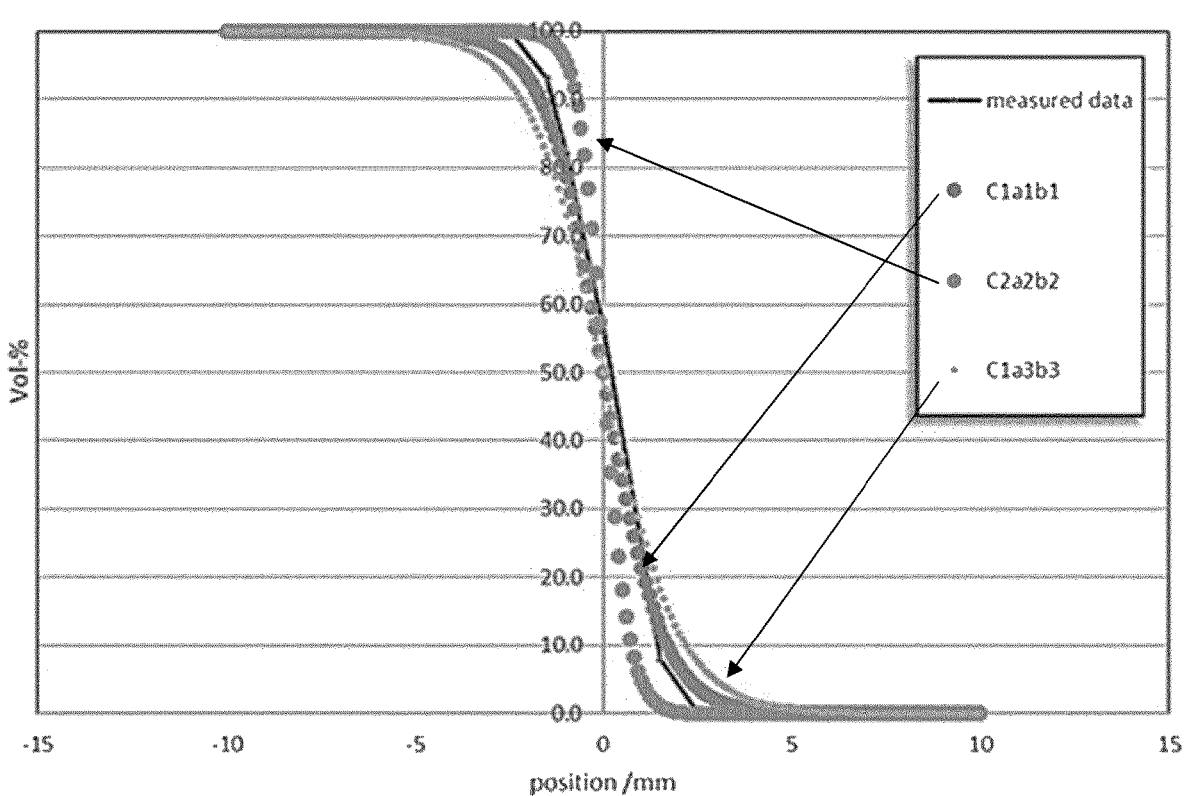
FIG. 14 shows a calculation-based approach of vol-% incisal powder in the transition zone.
Figure 15:
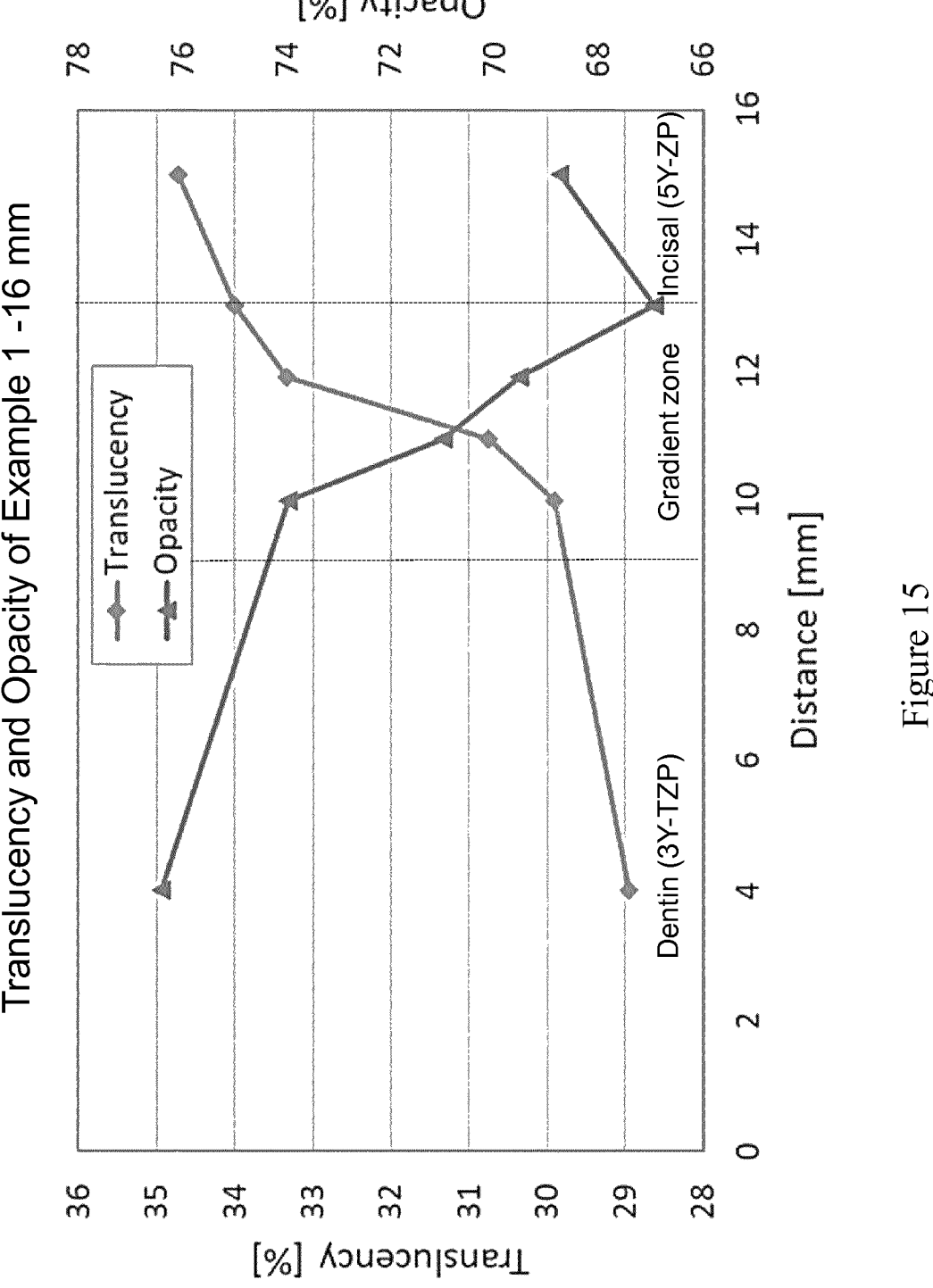
FIG. 15 shows a translucency gradient of Example 1 (disc height 16 mm). Thickness of samples is 1.0 mm.
Figure 17:
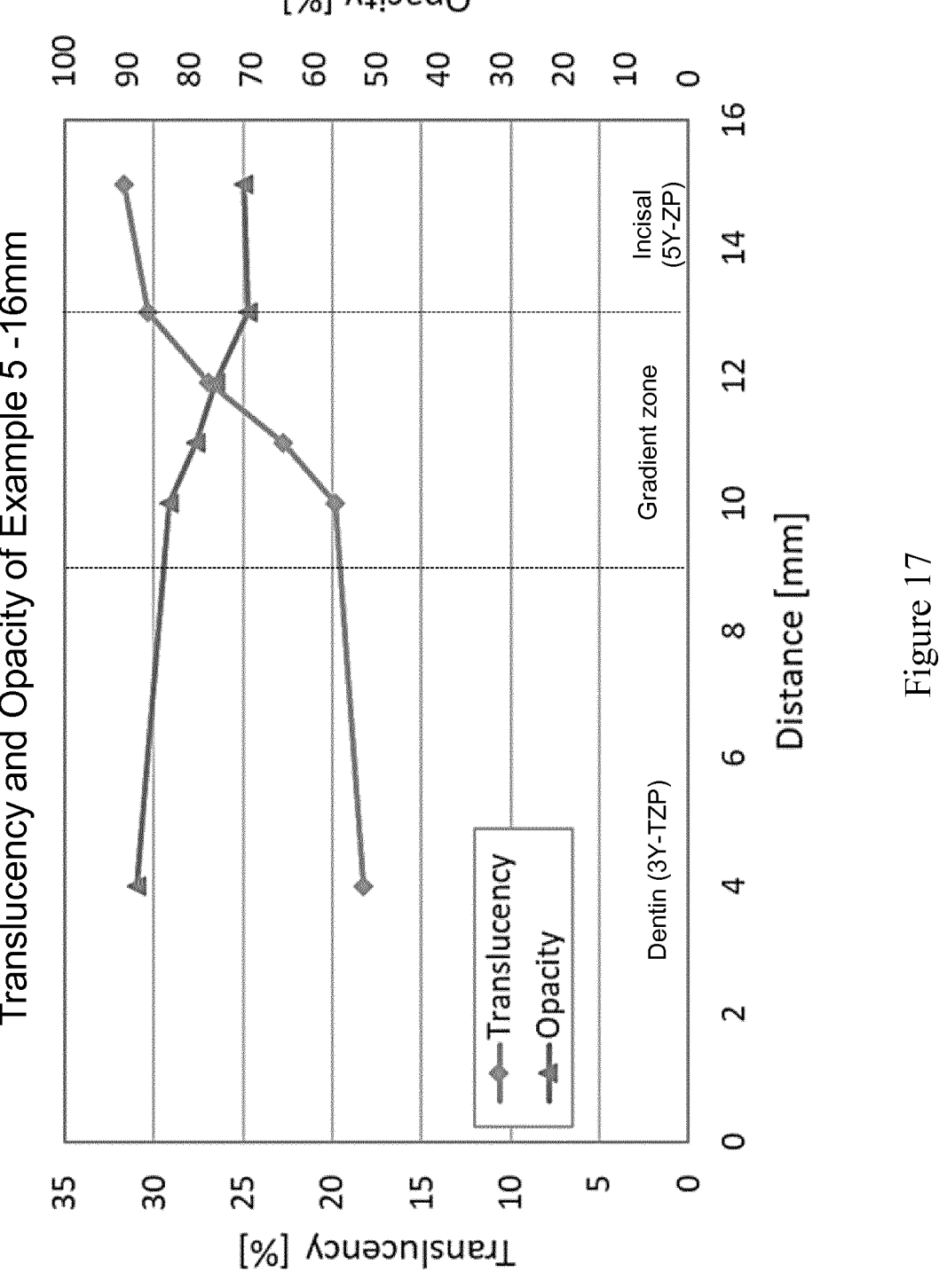
FIG. 17 shows a translucency gradient of Example 5 (disc height 16 mm). Thickness of samples is 1.0 mm.
Figure 19:
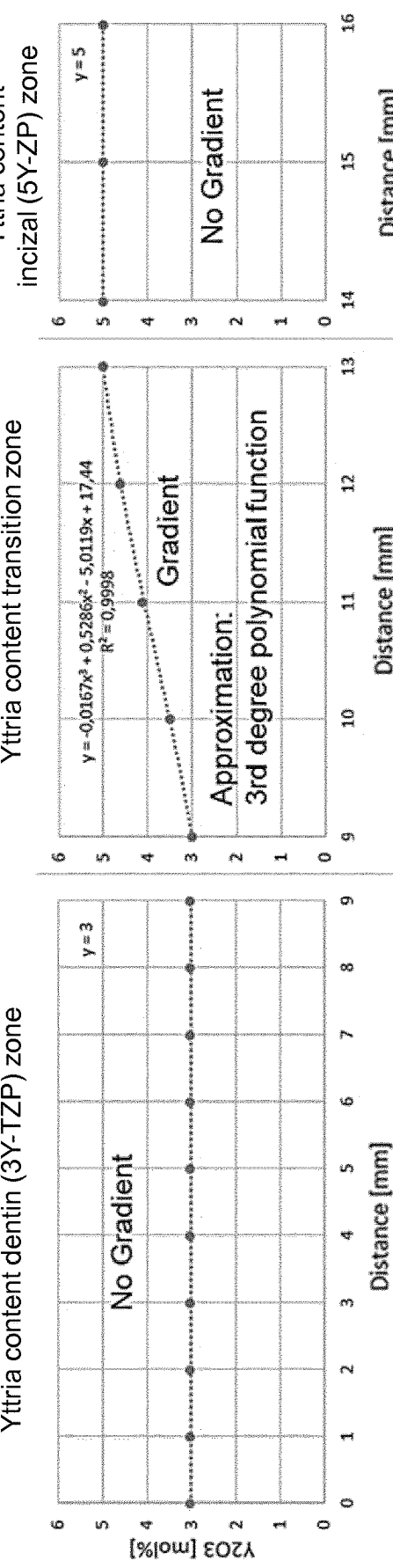
FIG. 19 shows $Y_2O_3$ content as a function of distance (disc height is 16 mm) using a polynomial function.
Figure 20:
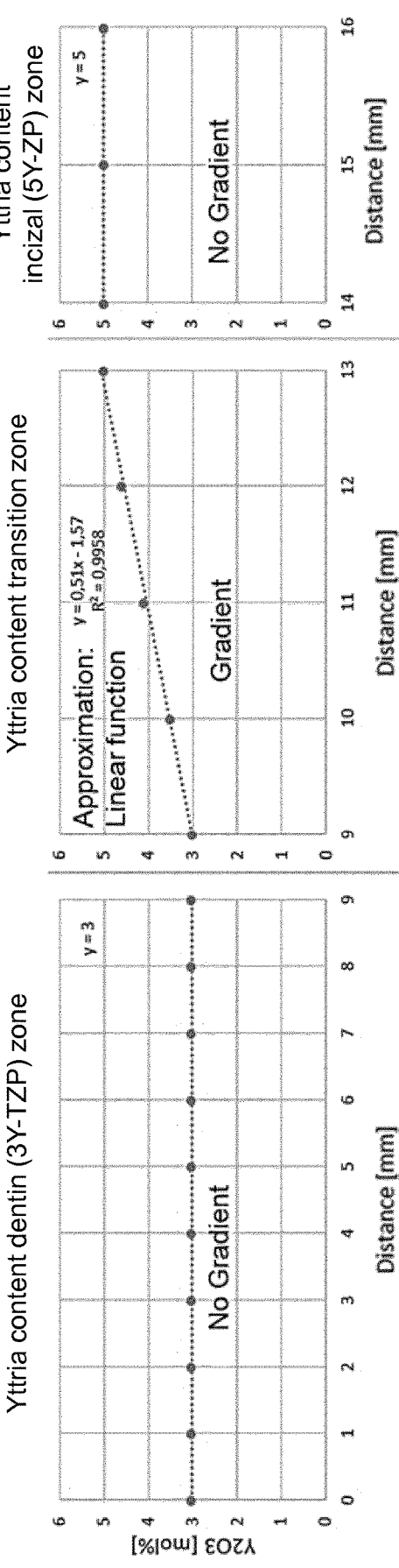
FIG. 20 shows $Y_2O_3$ content as a function of distance (disc height is 16 mm) using a linear function.
Figure 23:
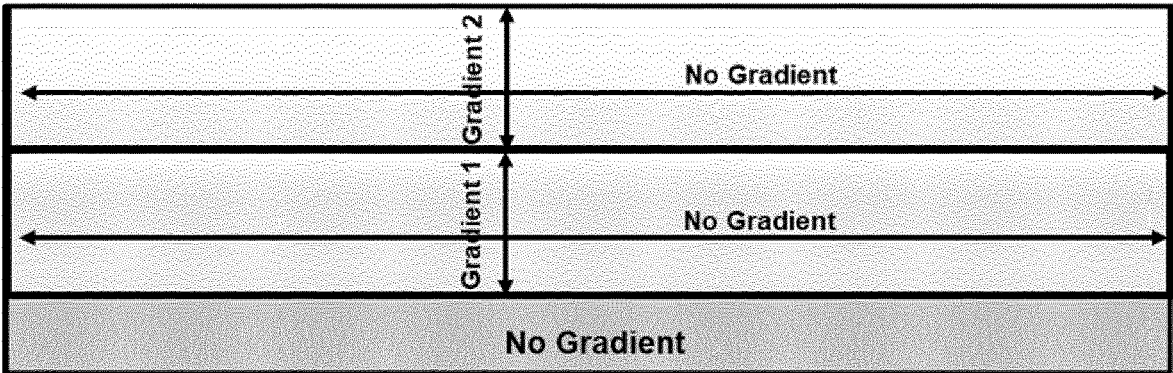
FIG. 23 shows various possibilities (types) wherein gradient- and no-gradient zones are of pre-sintered and sintered zirconia dental materials are combined.
Figure 24:
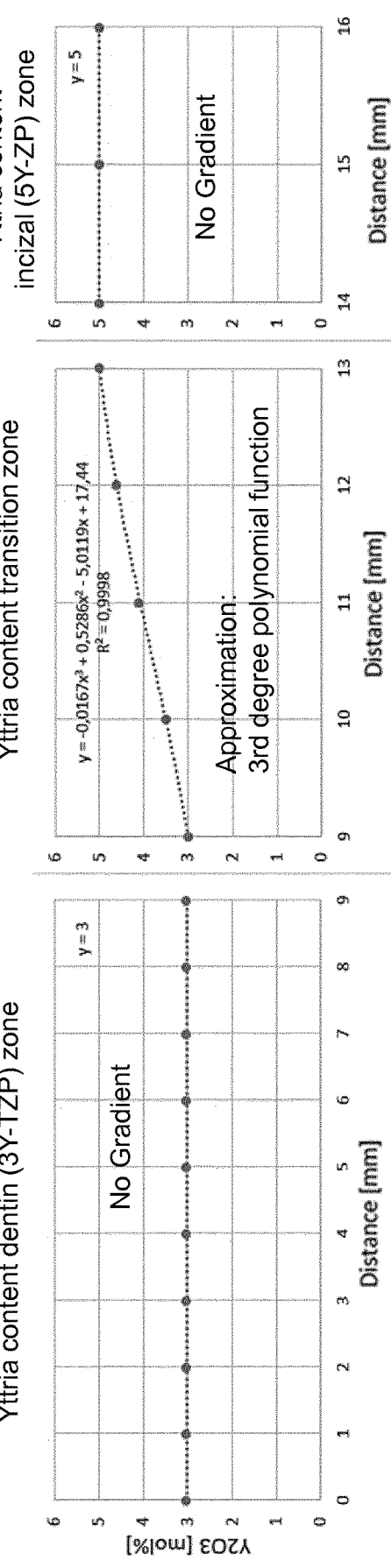
FIG. 24 shows an example of $Y_2O_3$ content as a function of distance (disc height 16 mm) and an example of a polynomial gradient function.
Figure 25:
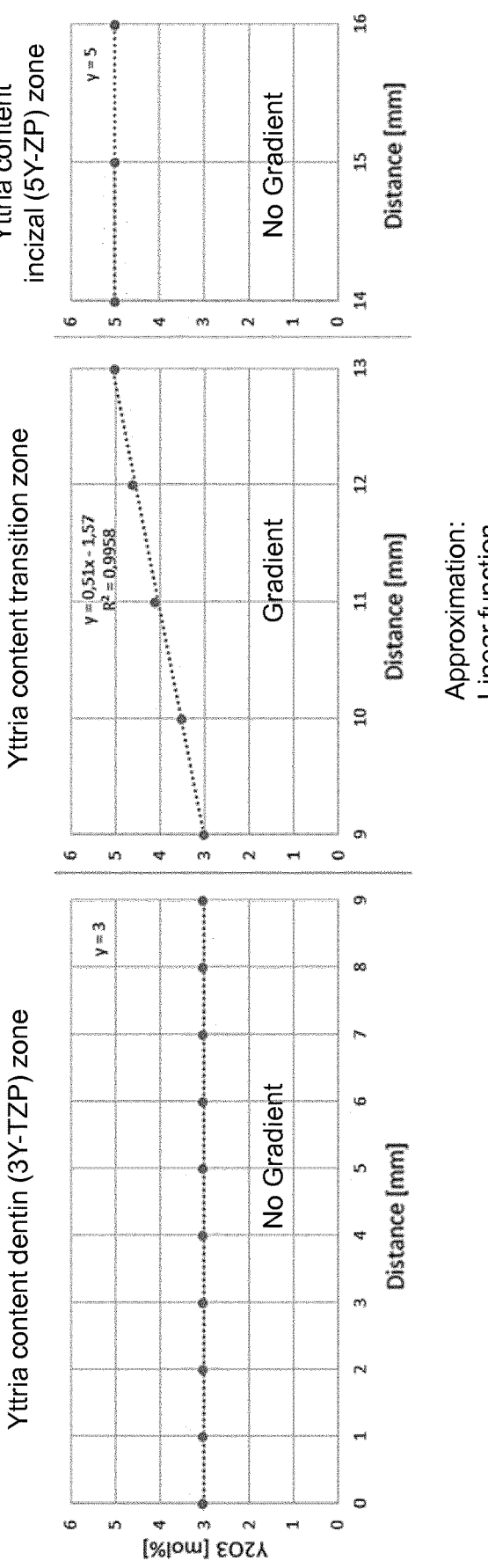
FIG. 25 shows an example of $Y_2O_3$ content as a function of distance (disc height 16 mm) and an example of a linear gradient function.

A sintered zirconia dental ceramic material may have non-linear yttria gradient or comprise at least one region (e.g., a transition zone) that is described or approximated by (e.g., defined by) one of the following functions (i.e., equations):

$y=ax+b$ (a linear gradient), where $a=0.05–3$, including all 0.001 values and ranges therebetween, and $b=-50–10$, including all 0.1 values and ranges therebetween, (e.g., $y=0.51x–1.57$) or $y=-0.0167x^3+0.5286x^2-5.0119x+17.44$ (a non-linear gradient), where y is the yttria content. In an example, this non-linear gradient is for 16 mm disc that is formed from pre-sintered zirconia dental ceramic formed from a mixture of 3Y-TZP and 5Y-ZP zirconia ceramic powders (e.g., as shown in FIG. 19).

A sintered zirconia dental ceramic may have (e.g., exhibit) one or more desirable physical/mechanical properties. A sintered zirconia dental ceramic (or a portion thereof) may exhibit gradient in the values of one or more physical/mechanical properties. In various examples, at least a portion or all of the sintered zirconia dental ceramic exhibit a gradient in fracture toughness or biaxial flexural strength or both fracture toughness or biaxial flexural strength. In various other examples, at least a portion of or all of the sintered zirconia dental ceramic exhibits a gradient in fracture toughness or biaxial flexural strength or both fracture toughness or biaxial flexural strength and a gradient in translucency and/or color.

A gradient of a physical/mechanical property or optical property may be a continuous and uninterrupted gradient. A gradient of a physical/mechanical property or optical property may not be discontinuous. A sintered zirconia dental ceramic material may have a linear or non-linear physical/mechanical property and/or optical property gradient. The gradient may be in a direction normal to a longest dimension of the pre-sintered zirconia dental ceramic material.

A sintered zirconia dental ceramic material may have different regions (which are also referred to herein as zones) with different physical/mechanical property and/or optical property gradients. An individual zone may have the same gradient as one or more of the other zones or each zone may have a different gradient. For example, the pre-sintered zirconia dental ceramic material comprises at least two or at least three zones where adjacent zones have different physical/mechanical property and/or optical property gradients.

In an example, the sintered zirconia dental ceramic has no region in which there is one or more physical/mechanical property and/or one or more optical property gradient having a dimension (e.g., a length) of 1 to 200 microns (or less than or equal to 10% of the ceramic (e.g., of the transition zone)) in a direction normal to the largest dimension of the ceramic that has a constant physical/mechanical property and/or optical property. In another example, the sintered zirconia dental ceramic has no region having a dimension (e.g., a length) of 1 to 300 microns or less than or equal to 10%, 5%, or 1% of the ceramic (e.g., of the transition zone)) in a direction normal to the largest dimension of the ceramic that has a constant physical/mechanical property and/or optical property.

A sintered zirconia dental ceramic material may have a physical/mechanical property and/or optical property gradient where the physical/mechanical property and/or optical property gradient increases or decreases along the gradient from the first outer surface to the second outer surface. In an example, the sintered zirconia dental ceramic has a first outer surface and a second outer surface opposite the first outer surface, and further comprising a yttria content between the first outer surface and the second outer surface, where the yttria content having a concentration of yttria that varies according to a gradient along a dimension from the first outer surface to the second outer surface, where the physical/mechanical property and/or optical property gradient is a linear gradient or a non-linear gradient.

A zirconia dental ceramic material may have non-linear physical/mechanical property and/or optical property gradient that is described or approximated by (e.g., defined by) a function (i.e., an equation) or a combination of functions. In non-limiting examples, the gradient is described or approximated by (e.g., defined by) the sum of two gradient functions (i.e., equations) chosen from linear gradients, non-linear gradients, and combinations thereof. Non-limiting examples of functions defining the non-linear gradient in physical/mechanical property and/or optical property in at least a portion or all of a sintered zirconia dental ceramic material include exponential functions, which may define an exponential gradient, first-order polynomial functions, which may define first order polynomial gradients, second-order polynomial functions, which may define second-order polynomial gradients, third-order polynomial functions, which may define third-order polynomial gradients, power law polynomial functions, which may define power law polynomial gradients, logarithmic (e.g., logarithm) functions, which may define logarithmic (e.g., logarithm) gradients, or the like, or a combination thereof.

The biaxial flexural strength of the sintered zirconia dental ceramic samples may be determined in accordance with ISO6872 using a piston on a three ball test. The fracture toughness of the sintered zirconia dental ceramic may be tested in accordance with ISO6872 guidelines for single edge V-notched beam method or a Vickers indentation fracture (IF) according to ISO 14627:2012. In a single edge V-notched beam method, the bars (3 mm×4 mm×17 mm) may be fabricated and prepared with a V-notch ranging from 0.8-1.2 mm. The hardness testing of the sintered zirconia dental ceramic may be determined in accordance with ISO14705 (e.g., ISO 14705:2008).

It would be understood by one of ordinary skill in the art that while ISO6872:2015, and ISO14705:2016 were the latest ISO test protocols available as of the preparation of this patent application, future and past versions of ISO6872 and ISO14705, while differing slightly, use essentially the same testing methods and any slight modifications in the official ISO6872 and ISO14705 over time would not change test results beyond an acceptable margin of error.

A sintered zirconia dental ceramic may have desirable optical properties. For example, at least a portion of a zirconia dental ceramic does not exhibit a gradient in translucency. In various examples, a sintered zirconia dental ceramic has a first outer surface and a second outer surface and along a dimension from the first outer surface to the second outer surface the translucency is substantially the same (e.g., not varying by more than 5%, more than 1%, or more than 0.1%). In an example, at least a portion of, a plurality of portions of, or all of the sintered zirconia ceramic material has a light transmittance at 560 nm wavelength of 40 to 60% for a 1 to 2 mm thick sample of the sintered zirconia ceramic material.

In the case of a sintered zirconia dental ceramic material having a plurality of zones, the transmittance may be different in at least two of the zones or at least three of the zones. In various examples, the color and/or biaxial flexural strength is different in each of the zones. In an example, a sintered zirconia dental ceramic material comprises a dentin zone having a transmittance (at 560 nm for a 1 to 2 mm thick sample of the sintered zirconia ceramic material of the dentin zone) of 15-35% (e.g., 17-20%) and/or an incisal zone having a transmittance (for a 1 to 2 mm thick sample of the sintered zirconia ceramic material of the incisal zone) of 25-40% (e.g., 30-35%) and/or a transition zone having a transmittance (for a 1 to 2 mm thick sample of the sintered zirconia ceramic material of the incisal zone) of 15-40%.

A sintered zirconia dental ceramic may have desirable translucency. For example, the sintered zirconia dental ceramic has a first outer surface and a second outer surface opposite to the first outer surface and along at least a portion or all of a dimension from the first outer surface to the second outer surface (e.g., moving from the dentin zone thru the transition zone and to the dentin zone) the translucency increases. For example, the translucency increases corresponding to a linear function (e.g., $y=3.575x-16.0012$). For example, the translucency increases corresponding to a non-linear function (e.g., a $3^{rd}$ degree polynomial function, such as, for example, $y=0.4374x^3+15.056x^2-168.28x+634.39$).

A sintered zirconia dental ceramic may have desirable biaxial flexural strength. For example, the sintered zirconia dental ceramic has a first outer surface and a second outer surface opposite to the first outer surface and along at least a portion or all of a dimension from the first outer surface to the second outer surface (e.g., moving from the dentin zone thru the transition zone and to the incisal zone) the biaxial flexural strength or average biaxial strength decreases. For example, the biaxial strength or average biaxial strength decreases corresponding to a linear function (e.g., $y=-189.47x+3314.7$) or a non-linear function.

A zirconia dental ceramic material may have desirable color. A zirconia dental ceramic material may the same or a plurality of colors. For example, a zirconia dental ceramic material has a plurality of zones and at least one of the zones may have a different color than the other zones or each zone may have a different colors. An individual color may be described by the commonly used CIE (Commission Internationale de l'Eclariage) L*, a*, b* conventions, which represents colors in a three-dimensional Cartesian coordinate system. L*, or "value", is a measure of luminance or lightness, and is represented on the vertical axis. The a* and b* coordinates, are a measure of chromaticity and are represented on the horizontal coordinates, with positive a* representing red, negative a* representing green, positive b* representing yellow and negative b* representing blue. U.S. Pat. No. 6,030,209, the disclosure color description in which is incorporated herein by reference, discusses the CIE L*, a*, b* color coordinates of tooth colors represented by the Vita Lumen® shade guide system manufactured by Vita Zahnfabrik. It provides the color space of tooth colors. Herein, "color," unless otherwise indicated, is taken to mean CIE L*, a*, b* color coordinates that fall within or substantially within this color space. Multiplicity of colors of natural dentition exclusive of incisal and dentin areas can be quantitatively described as belonging to color space delineated by L* from about 60 to about 100, a* from about −3 to about +10, and b* from about 2 to about 36.

For example, the sintered zirconia dental ceramic has a first outer surface and a second outer surface opposite to the first outer surface and along at least a portion or all of a dimension from the first outer surface to the second outer surface (e.g., moving from the dentin zone thru the transition zone and to the incisal zone) the color changes. For example, the L* brightness value increases corresponding to a linear function (e.g., $y=2.1081x+59.871$) or a non-linear function (e.g., a $3^{rd}$ degree polynomial function, such as, for example, $y=-0.1595x^3+5.5218x^2-61.295x+301.027$, or an exponential function, such as, for example, $y=63.028e^{0.0251x}$) and/or the a* value decreases corresponding to a linear function (e.g., $y-1.7045x+22.681$) or a non-linear function (e.g., a $3^{rd}$ degree polynomial function, such as, for example, $y=0.1135x^3-3.9863x^2+44.714x-156.49$ and/or the b* value decreases corresponding to a linear function (e.g., $y=-1.7136x+39.511$) or a non-linear function (e.g., a $3^{rd}$ degree polynomial function, such as, for example, $y=0.1817x^3--6.5495x^2+76.468x-269.4$.

The sintered zirconia dental ceramic may have desirable microstructure. For example, the sintered zirconia dental ceramic has a first outer surface and a second outer surface opposite to the first outer surface and along at least a portion or all of a dimension from the first outer surface to the second outer surface (e.g., moving from the dentin zone thru the transition zone and to the incisal zone) the grain size increases. For example, the grain size increases corresponding to a linear function (e.g., $y=0.1765-1.2488$). For example, the grain size increases corresponding to a non-linear function (e.g., a $3^{rd}$ degree polynomial function, such as, for example, $y=0.0037x^3+0.0934x^2-0.5318x+0.1885$).

In the case of a sintered zirconia dental ceramic material having a plurality of zones, the color and/or translucency and/or biaxial flexural strength may be different in at least two of the zones or at least three of the zones. In various examples, the color and/or translucency and/or biaxial flexural strength is different in each of the zones. In various examples, the function(s) describing the yttria composition and/or color and/or translucency, in at least a portion (e.g., the portion between an incisal zone and/or dentin zone and the immediately adjacent transition zone) or all of sintered zirconia dental material (or a dental article), in a direction normal to the longest dimension of the material or article, is/are not discontinuous. In various examples, a sintered zirconia dental ceramic material has a first zone (which may be an incisal zone) having a biaxial flexural strength in the range of 500-1200 MPa (e.g., 600-800 MPa or 1000-1200 MPa), including all integer MPa values and ranges therebetween, and second zone which may be an dentin zone) having a biaxial flexural strength in the range of 800-1700 MPa (e.g., 850-1200 MPa or 1400-1700 MPa), including all integer MPa values and ranges therebetween, and a transition zone having a biaxial flexural strength in the range of 600-1400 MPa (e.g., 700-1000 MPa or 1100-1400 MPa), including all integer MPa values and ranges therebetween. In these examples, the biaxial flexural strength of the second zone may be greater than the biaxial flexural strength of the first zone. In these examples, the translucency of the first zone may be higher than the translucency of the second zone.

The sintered zirconia dental ceramic materials can have various form factors. In non-limiting examples, a sintered zirconia dental ceramic is in the form of a dental article, dental restoration, or dental crown or the like.

A zirconia dental ceramic material (or a dental article) may not be a multilayer structure. In various examples, a zirconia dental ceramic (or a dental article) not exhibit discrete layer(s). A discrete layer may be observed by optical methods (e.g., optical microscopy). In various examples, a zirconia dental ceramic material (or a dental article) does not have one or more discrete layer (e.g., a layer comprising a constant yttria content) that is observable by visual inspection or optical microscopy (e.g., observable using a microscope at a magnification of 30×, 25×, 20×, 15×, 10×, 5×, 2× or the naked eye).

In an aspect, the present disclosure provides dental articles. A dental article of the present disclosure may be made by a method of the present disclosure. In various examples, a dental article is made using a pre-sintered zirconia dental ceramic material of the present disclosure. In various examples, a dental article comprises (or is formed of) sintered zirconia dental ceramic material of the present disclosure.

A dental article may have various form factors. In various examples, the dental article is a blank or smart blank. In various other examples, the dental article is a dental restoration. Non-limiting examples of dental restorations include full-contour FPDs (fixed partial dentures), bridges, implant bridges, multi-unit frameworks, abutments, crowns, partial crowns, veneers, inlays, onlays, orthodontic retainers, space maintainers, tooth replacement appliances, splints, dentures, posts, teeth, jackets, facings, facets, implants, cylinders, connectors, and the like. A smart blank is a pre-form or a near net shape CAD/CAM milling blank, which may be used for fabrication of dental restorations described herein.

A dental article may have (e.g., exhibit) one or more desirable physical/mechanical property and/or one or more desirable optical property. The desirable physical/mechanical property(ies) and/or one or more desirable optical property(ies) are as described above for sintered zirconia dental ceramic materials.

The steps of the method described in the various embodiments and examples disclosed herein are sufficient to carry out the methods of the present disclosure. Thus, in an example, a method consists essentially of a combination of the steps of the methods disclosed herein. In another example, a method consists of such steps.

The following example is presented to illustrate the present disclosure. It is not intended to be limiting in any matter.

Example 1

This example provides a description of examples of pre-sintered zirconia dental ceramic materials and dental articles of the present disclosure. This example also describes characterization of the pre-sintered zirconia dental ceramic materials and dental articles and methods of making the pre-sintered dental zirconia dental ceramic materials.

FIGS. 1-38 describe various compositional features, structural features, and properties of examples (Examples 1-5) of pre-sintered zirconia dental materials and sintered zirconia dental materials of the present disclosure. The Example materials were prepared using methods described herein using 3Y-TZP and 5Y-ZP zirconia ceramic powders.

Fracture resistance was determined using Vickers indentation fracture (IF) according to ISO 14627:2012. In the case of 3Y-TZP derived materials, a test force of HV 20 resp. a load of 196.13 N was used. In the case of 5Y-ZP derived materials we used a test force of HV 5 resp. a load of 49.03 N. Vickers hardness was determined according to ISO 14705:2008.

TABLE 1

Dentin/incisal distribution in an example of a pre-sintered zirconia dental ceramic of the present disclosure.

| Disc height | 14 [mm] | 100 [%] | 16 [mm] | 100 [%] | 20 [mm] | 100 [%] | 25 [mm] | 100 [%] |
|---|---|---|---|---|---|---|---|---|
| Incisal zone | 3 | 21.43 | 3 | 18.75 | 3 | 15 | 3 | 12 |
| Transition zone | 4 | 28.57 | 4 | 25.00 | 4 | 20 | 4 | 16 |
| Dentin zone | 7 | 50.00 | 9 | 56.25 | 13 | 65 | 18 | 72 |

TABLE 2

Gradient (b * values) of IPS e. max ZirCAD Prime BL1 (# X47908) and A3 (# Y03720).

|  | BL1 | A3 |
|---|---|---|
| Dentin | 4.96 | 22.21 |
| Transition zone 1 | 4.80 | 22.02 |
| Transition zone 2 | 4.46 | 21.17 |
| Transition zone 3 | 4.08 | 19.28 |
| Transition zone 4 | 3.81 | 17.00 |
| Incisal | 3.84 | 16.53 |

Although the present disclosure has been described with respect to one or more particular embodiments and/or examples, it will be understood that other embodiments and/or examples of the present disclosure may be made without departing from the scope of the present disclosure.

The invention claimed is:

1. A pre-sintered zirconia dental ceramic material having a linear gradient or non-linear gradient that is continuous and uninterrupted in yttria content in at least a portion or all of the pre-sintered zirconia dental ceramic material, wherein the gradient is defined by the following equation:

$$y = ax + b, \text{ wherein } a \text{ is } 0.05 \text{ to } 3, \text{ and } b \text{ is } -50 \text{ to } 10$$
or $$y = -0.0167x^3 + 0.5286x^2 - 5.0119x + 17.44, \text{ wherein } y \text{ is the yttria content.}$$

2. The pre-sintered zirconia dental ceramic material of claim 1, wherein the pre-sintered zirconia dental ceramic has a first outer surface and a second outer surface opposite the first outer surface, and further comprising a yttria content between the first outer surface and the second outer surface, the yttria content having a concentration of yttria that varies according to a gradient along a dimension from the first outer surface to the second outer surface, wherein the gradient is a linear or non-linear gradient.

3. The pre-sintered zirconia dental ceramic material of claim 1, wherein the linear gradient or non-linear gradient is an exponential gradient, a first order polynomial gradient, a second order polynomial gradient, a third-order polynomial gradient, a power law gradient, a logarithm gradient, or a combination thereof.

4. The pre-sintered zirconia dental ceramic material of claim 2, wherein the yttria concentration increases along the gradient from the first outer surface to the second outer surface.

5. The pre-sintered zirconia dental ceramic material of claim 1, wherein the gradient is the sum of two exponential gradient functions.

6. The pre-sintered zirconia dental ceramic material of claim 1, wherein the pre-sintered zirconia dental ceramic material comprises at least two adjacent gradient zones with different gradients.

7. The pre-sintered zirconia dental ceramic material of claim 1, wherein the yttria content is 2 to 8 mol %.

8. The pre-sintered zirconia dental ceramic material of claim 1, wherein the yttria content is formed from a mixture of two yttria-containing zirconia materials.

9. The pre-sintered zirconia dental ceramic material of claim 8, wherein the pre-sintered zirconia dental ceramic has a first outer surface and a second outer surface opposite the first outer surface, and along a dimension from the first outer surface to the second outer surface the color that is substantially the same.

10. The pre-sintered zirconia dental ceramic material of claim 1, wherein the pre-sintered zirconia dental ceramic is in the form of a disk, a block, blank, preformed dental restoration, or preformed dental appliance.

11. The pre-sintered zirconia dental ceramic material of claim 1, wherein the pre-sintered zirconia dental ceramic has at least one dimension of 10 to 30 mm.

12. The pre-sintered zirconia dental ceramic material of claim 1, wherein the pre-sintered zirconia dental ceramic comprises two or more zones or three or more zones.

13. The pre-sintered zirconia dental ceramic material of claim 12, wherein the gradient yttria content is different in at least two of the zones or at least three of the zones.

14. The pre-sintered zirconia dental ceramic material of claim 12, wherein the gradient yttria content is different in each of the zones.

15. The pre-sintered zirconia dental ceramic material of claim 12, wherein the pre-sintered zirconia dental ceramic comprises an incisal zone, a transition zone, and a dentin zone.

16. A method of making the pre-sintered zirconia dental ceramic material having a linear gradient or non-linear gradient that is continuous and uninterrupted in yttria content in at least a portion or all of the pre-sintered zirconia dental ceramic material of claim 1 comprising:

forming a monolithic structure from at least a first zirconia ceramic powder having a first yttria content and a second zirconia ceramic powder having a second yttria content, wherein the first yttria content is different than the second yttria content;

subjecting the monolithic structure to uniaxial pressing at a pressure of 75-100 MPa;

subjecting the uniaxially pressed monolithic structure to cold isotactic pressing at a pressure of 200-400 MPa; and heating the uniaxial pressed and cold isostatic pressed monolithic structure to a temperature of 900-1100° C., wherein the pre-sintered zirconia dental ceramic material is formed.

17. The method of claim 16, wherein one or more or all of the zirconia ceramic powders is/are in granulate form and the granules are brought into contact with a solution that contains metal ions and/or metal complexes.

18. The method of claim 16, wherein one or more of the zirconia ceramic powder(s) comprises lanthanum ions.

19. The method of claim 16, wherein at least one zirconia ceramic powder(s) comprises lanthanum ions and at least one different zirconia ceramic powder comprise magnesium ions and/or aluminum ions.

20. The method of claim 16, wherein the monolithic structure is formed by mixing 5Y zirconia ceramic powder and 3Y zirconia ceramic powder in a selected ratio to form a transition zone.

21. The method of claim 16, wherein the monolithic structure has a first outer surface and a second outer surface and along at least or portion or all of dimension from the first outer surface to the second outer surface the gradient yttria content is a linear gradient.

22. The method of claim 16, wherein the monolithic structure has a first outer surface and a second outer surface and along at least or portion or all of dimension from the first outer surface to the second outer surface the gradient yttria content is a non-linear gradient.

23. The method of claim 16, wherein the gradient yttria content is an exponential gradient, a first order polynomial gradient, a second order polynomial gradient, a third-order polynomial gradient, a power law gradient, a logarithm gradient, or a combination thereof.

24. The method of claim 16, wherein the pre-sintered zirconia dental ceramic has a first outer surface and a second outer surface and along at least or portion or all of dimension from the first outer surface to the second outer surface the yttria concentration increases.

25. The method of claim 16, wherein the gradient yttria content is the sum of two exponential gradient functions chosen from linear gradients, non-linear gradients, and combinations thereof.

26. The method of claim 16, wherein the yttria content gradient is described by or approximated by the following equation:

$y=ax+b$, wherein $a$ is 0.05–3, and $b$ is −50–10 or $y=-0.0167x^3+0.5286x^2-5.0119x+17.44$, wherein $y$ is the yttria content.

27. The method of any claim 16, wherein the yttria content is 2 to 8 mol %.

28. The method of claim 16, wherein the zirconia ceramic powders are independently chosen from 1.5Y to 10Y.

29. The method of claim 16, wherein the first zirconia ceramic powder having a first yttria content is 3Y-TZP and the second zirconia ceramic powder having a second yttria content is 5Y-ZP.

30. The method of claim 16, wherein one or more or all of the zirconia ceramic powder(s) has/have less than 1% by weight of particles having a of greater than 400 microns.

31. The method of claim 16, wherein one or more or all of the zirconia ceramic powder(s) has/have less than 1% by weight of particles having a size of greater than 200 microns.

32. The pre-sintered zirconia dental ceramic material of claim 1, wherein the pre-sintered zirconia dental ceramic comprises one or more coloring additives selected from the lanthanide series of elements and compounds thereof, excluding synthetic and radioactive elements, groups 5 to 11 of the periodic table and compounds thereof, excluding synthetic and radioactive elements, and Ti, Sc and compounds thereof.

33. A dental article formed from a pre-sintered zirconia dental ceramic material of claim 32.

* * * * *